United States Patent
Sufi et al.

(10) Patent No.: US 11,987,785 B2
(45) Date of Patent: *May 21, 2024

(54) MICROELECTRODE TECHNIQUES FOR ELECTROPORATION

(71) Applicant: Ravata Solutions, Inc., Davis, CA (US)

(72) Inventors: Gurkern Sufi, Sacramento, CA (US); Arshia Firouzi, Folsom, CA (US)

(73) Assignee: RAVATA SOLUTIONS, INC., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/850,248

(22) Filed: Jun. 27, 2022

(65) Prior Publication Data
US 2023/0079005 A1 Mar. 16, 2023

Related U.S. Application Data

(63) Continuation of application No. 16/607,689, filed as application No. PCT/US2018/029649 on Apr. 26, 2018, now Pat. No. 11,371,004.

(Continued)

(51) Int. Cl.
*C12M 1/42* (2006.01)
*B01J 19/08* (2006.01)
*C12N 13/00* (2006.01)

(52) U.S. Cl.
CPC .............. *C12M 35/02* (2013.01); *B01J 19/08* (2013.01); *C12N 13/00* (2013.01)

(58) Field of Classification Search
CPC ....... C12M 35/02; C12M 41/48; C12N 13/00; B01J 19/08
See application file for complete search history.

(56) References Cited

U.S. PATENT DOCUMENTS

| 5,137,817 A | 8/1992 | Busta et al. |
| 6,300,108 B1 | 10/2001 | Rubinsky et al. |

(Continued)

FOREIGN PATENT DOCUMENTS

| CN | 1280513 A | 1/2001 | |
| WO | WO-03071140 A2 * | 8/2003 | ............ C12M 41/46 |

OTHER PUBLICATIONS

Battye et al., (2000). "Single cell sorting and cloning," Journal of Immunological Methods 243:25-32.

(Continued)

*Primary Examiner* — Michael L Hobbs
(74) *Attorney, Agent, or Firm* — Morrison & Foerster LLP

(57) ABSTRACT

A microelectrode for electroporating an individual cell or embryo that includes a substrate with an electrically insulated surface, a first electrode adjacent to the electrically insulated surface of the substrate, a second electrode adjacent to the electrically insulated surface of the substrate and separated from the first electrode a predetermined distance so as to form a channel, and a liquid medium situated within the channel. The liquid medium is capable of fluidic transport of the cell or embryo through or into the channel and capable of supporting an electric field. The first and second electrodes include surfaces substantially orthogonal to the electrically insulated surface of the substrate with an edge length that is less than or equal to a diameter of the cell or embryo. The predetermined distance may be 50% to 200% of the diameter of the cell or embryo.

14 Claims, 7 Drawing Sheets

Related U.S. Application Data

(60) Provisional application No. 62/490,486, filed on Apr. 26, 2017.

(56) References Cited

U.S. PATENT DOCUMENTS

| | | | |
|---|---|---|---|
| 6,387,671 | B1 | 5/2002 | Rubinsky et al. |
| 7,358,077 | B2 | 4/2008 | Zimmermann et al. |
| 8,058,056 | B2 | 11/2011 | Lee et al. |
| 9,034,661 | B2 | 5/2015 | Kusaki et al. |
| 9,121,806 | B1 | 9/2015 | Bhansali et al. |
| 9,200,270 | B2 | 12/2015 | Hsieh et al. |
| 9,377,456 | B1 | 6/2016 | Herget et al. |
| 11,371,004 | B2 * | 6/2022 | Sufi .................. C12M 41/48 |
| 2008/0081372 | A1 | 4/2008 | Huang |
| 2008/0153146 | A1 | 6/2008 | Stett et al. |
| 2009/0317883 | A1 * | 12/2009 | Ragsdale .............. C12M 35/02 435/173.6 |
| 2012/0135887 | A1 | 5/2012 | Lee et al. |
| 2014/0113356 | A1 | 4/2014 | Tseng et al. |
| 2014/0323351 | A1 | 10/2014 | Zhu et al. |
| 2016/0102282 | A1 * | 4/2016 | Choi .................. C12M 35/02 435/289.1 |
| 2016/0215297 | A1 | 7/2016 | Kaneko et al. |

OTHER PUBLICATIONS

Garbison et al., (2012). "Impedance-Based Technologies," Assay Guidance Manual, pp. 1-9.

Geng et al., (2011). "Transfection of cells using flow-through electroporation based on constant voltage," Nature Protocols 6(8):1192-1208.

International Preliminary Report dated Nov. 7, 2019, for PCT Patent Application No. PCT/US2018/029649 filed on Apr. 26, 2018, 10 pages.

International Search Report and Written Opinion dated Jul. 19, 2018, for PCT Patent Application No. PCT/US18/29649 filed on Apr. 26, 2018, 17 pages.

Knox et al., (2013). "A streamlined implementation of the glutamine synthetase-based protein expression system," BMC Biotechnology, 13(74):1-10.

Kurz et al., (2014). "Single Cell Transfection with Single Molecule Resolution Using a Synthetic Nanopore," Nano Lett., 14:604-611.

Love et al., (2013). "Microtools for single-cell analysis in biopharmaceutical development and manufacturing," Trends in Biotechnology, 31(5):280-286.

Nakamura et al., (2015), "Optimization of cell line development in the GS-CHO expression system using a high-throughput, single cell-based clone selection system," Journal of Bioscience and Bioengineering, 120(3):323-329.

Sanchez-Garcia et al., (2016). "Recombinant pharmaceuticals from microbial cells: a 2015 update," Microb Cell Fact, 15(33):1-7.

Wang et al., (2010). "A DEP-Assisted Single-Cell Electroporation Chip with Low Operation Voltage," IEEE Sensors 2010 Conference, pp. 2097-2100.B28.

Zhang et al., (2005). "New Technologies in Tumor Physical Therapy," People's Military Medical Press, 84-86. English abstract.

* cited by examiner

MICROELECTRODE TECHNIQUES FOR ELECTROPORATION

CROSS REFERENCE TO RELATED APPLICATIONS

This application is a continuation of U.S. application Ser. No. 16/607,689, which granted on Jun. 28, 2022 as US11,371,004, which is a U.S. National Phase patent application under 35 U.S.C. § 371 of International Application No. PCT/US2018/029649, filed internationally on Apr. 26, 2018, which claims the priority benefit of U.S. Provisional Application Ser. No. 62/490,486, filed Apr. 26, 2017, the disclosures of which is are incorporated herein by reference in its their entirety.

BACKGROUND

Field

The present disclosure generally relates to permeabilization of cell or embryo membrane by electroporation, and more specifically to a microelectrode used to control the effects of electroporation across the cell or embryo membrane and sense a degree of permeabilization.

Description of Related Art

Traditionally, electroporation has been realized by applying an electric field over an entire surface of a cell or embryo, which induces pore formation of the membrane over the whole surface of the cell or embryo. To a certain degree this effect of electroporation has been found effective for safely delivering tiny molecules into cells. However, as the strength of the electric field increases, pores of the membrane rupture and merge with adjacent pores to form larger and larger pores. If the pores are induced to become too large, the process is termed "irreversible electroporation," where the ruptures to the membrane of the cell or embryo suffer irreversible damage and cannot be repaired, which results in cellular or embryonic death. This presents challenges for safely delivering large molecules into cells or embryos using electroporation while maintaining healthy cell populations.

BRIEF SUMMARY

The following presents a simplified summary of one or more examples in order to provide a basic understanding of such examples. This summary is not an extensive overview of all contemplated examples, and is intended to neither identify key or critical elements of all examples nor delineate the scope of any or all examples. Its purpose is to present some concepts of one or more examples in a simplified form as a prelude to the more detailed description that is presented below.

In accordance with some examples, a microelectrode for electroporating an individual cell or embryo, the microelectrode comprising: a substrate with an electrically insulated surface; a first electrode adjacent to the electrically insulated surface of the substrate, wherein the first electrode includes a first surface with an edge length that is less than or equal to a diameter of the cell or embryo, the first surface being substantially orthogonal to the electrically insulated surface of the substrate; a second electrode adjacent to the electrically insulated surface of the substrate and separated from the first electrode a predetermined distance so as to form a channel, wherein the second electrode includes a second surface with an edge length that is less than or equal to a diameter of the cell or embryo, the second surface being substantially orthogonal to the electrically insulated surface of the substrate; and a liquid medium situated within the channel, wherein the liquid medium is capable of fluidic transport of the cell or embryo through or into the channel and capable of supporting an electric field.

In some examples the microelectrode further comprises: a second substrate with a second electrically insulated surface situated above the channel, wherein the second electrically insulated surface being substantially parallel to the first electrically insulated surface and being separated from the first electrically insulated surface a second predetermined distance that is 100% to 250% or preferably 50% to 200% of the diameter of the cell or the embryo to position the cell or embryo within the channel between the first electrode and the second electrode. In some examples the microelectrode further comprises: a third electrode adjacent to the electrically insulated surface of the substrate; and a fourth electrode adjacent to the electrically insulated surface of the substrate, wherein the third electrode and the fourth electrode are situated adjacent to the channel or within the channel to accommodate electrical contact between the third electrode and the fourth electrode and the cell or embryo.

In accordance with some examples, an electroporation system comprising: a microelectrode for electroporating an individual cell or embryo, the microelectrode comprising: a substrate with an electrically insulated surface; a first electrode adjacent to the electrically insulated surface of the substrate, wherein the first electrode includes a first surface with an edge length that is less than or equal to a diameter of the cell or embryo, the first surface being substantially orthogonal to the electrically insulated surface of the substrate; a second electrode adjacent to the electrically insulated surface of the substrate and separated from the first electrode a predetermined distance so as to form a channel, wherein the second electrode includes a second surface with an edge length that is less than or equal to a diameter of the cell or embryo, the second surface being substantially orthogonal to the electrically insulated surface of the substrate; and a liquid medium situated within the channel, wherein the liquid medium is capable of fluidic transport of the cell or embryo through or into the channel and capable of supporting an electric field; and a first signal generator electrically coupled to the first electrode and the second electrode, wherein the first signal generator is configured to generate a signal between the first electrode and the second electrode that induces a uniform electric field with substantially parallel electric field lines between the first surface and the second surface.

In some examples the electroporation system further comprises: a switch electrically coupled to the first electrode and the second electrode, wherein the switch is configured to suppress an electric field between the first surface and the second surface in a first mode and provide an electric field between the first surface and the second surface in a second mode. In some examples the electroporation system further comprises a signal generator across the two electrodes wherein upon the prompting of a controller or computing system is configured to deliver an electric pulse between the first electrode and the second electrode. In some examples the signal generator is a monostable multivibrator. In some examples the signal generator is a tool that can be controlled by a controller or computer and can generate an electric pulse. In any of the disclosed embodiments, the pulse may be a square wave pulse, an exponential pulse, a sawtooth pulse, or other waveforms. In some examples the electroporation system further comprises: a second signal generator electrically coupled to the third electrode and the fourth electrode, wherein the second signal generator is configured to inject a signal at the third electrode. In some examples the signal generator is coupled to the first electrode and second electrode. In some examples the first and second electrodes are used to perform both electroporation and sensing. In some examples the electroporation system further comprises: a signal extractor electrically coupled to either the third electrode or the fourth electrode, wherein the signal extractor is configured to capture a signal response from the injected signal at the third electrode if coupled to the fourth electrode and at the fourth electrode if coupled to the third electrode.

In accordance with some examples, a method, comprising: configuring a microelectrode for electroporating an individual cell or embryo, the microelectrode comprising: a substrate with an electrically insulated surface; a first electrode adjacent to the electrically insulated surface of the substrate, wherein the first electrode includes a first surface with an edge length that is less than or equal to a diameter of the cell or embryo, the first surface being substantially orthogonal to the electrically insulated surface of the substrate; a second electrode adjacent to the electrically insulated surface of the substrate and separated from the first electrode a predetermined distance so as to form a channel, wherein the second electrode includes a second surface with an edge length that is less than or equal to a diameter of the cell or embryo, the second surface being substantially orthogonal to the electrically insulated surface of the substrate; and a liquid medium situated within the channel, wherein the liquid medium is capable of fluidic transport of the cell or embryo through or into the channel and capable of supporting an electric field; determining a permeability threshold, wherein the permeability threshold corresponds to a minimum amount of electrical energy applied to the cell or embryo at which cell membrane permeability is detected; applying a signal between the first electrode and the second electrode at the permeability threshold; injecting, at a third electrode, a signal; extracting, at a fourth electrode, a response to the injected signal, wherein the cell or embryo is electrically coupled between the third electrode and the fourth electrode; and storing the signal response in a non-transitory computer readable-medium. In some examples the method further comprises extracting the signal at the third electrode, or at the first electrode or the second electrode, wherein a switching circuit connects a pulse generator (e.g. a monostable multivibrator) to the electrode, a pulse is delivered by the pulse generator, after which the electrodes switch to connecting to the sensor module following which sensing signals and signal extraction are applied and executed.

In some examples the method further comprises: conditioning the extracted signal response. In some examples, determining the permeability threshold comprises: applying a first test signal between the first electrode and the second electrode at a predetermined electrical energy level; injecting, at the third electrode, a second test signal while the first test signal is being applied; extracting, at the fourth electrode, a response to the second test signal; determining whether the response to the second test signal is characteristic of membrane permeability of the cell or embryo; and in accordance with a determination that the response to the second test signal is characteristic of membrane permeability of the cell or embryo, storing electrical parameters associated with the predetermined electrical energy level. In some examples the method further comprises: conditioning the extracted second test signal response. In some examples, determining the permeability threshold further comprises: in accordance with a determination that the response to the second test signal is uncharacteristic of membrane permeability of the cell or embryo: iteratively adjusting the predetermined electrical energy level of the signal between the first electrode and the second electrode until a determination that the response to the second test signal is characteristic of membrane permeability of the cell or embryo; and storing electrical parameters associated with the adjusted predetermined electrical energy level.

1. A microelectrode for electroporating an individual cell or embryo, the microelectrode comprising:
    a substrate with an electrically insulated surface;
    a first electrode adjacent to the electrically insulated surface of the substrate, wherein the first electrode includes a first surface with an edge length that is less than or equal to a diameter of the cell or embryo, the first surface being substantially orthogonal to the electrically insulated surface of the substrate;
    a second electrode adjacent to the electrically insulated surface of the substrate and separated from the first electrode a predetermined distance so as to form a channel, wherein the second electrode includes a second surface with an edge length that is less than or equal to a diameter of the cell or embryo, the second surface being substantially orthogonal to the electrically insulated surface of the substrate; and
    a liquid medium situated within the channel, wherein the liquid medium is capable of fluidic transport of the cell or embryo through or into the channel and capable of supporting an electric field.
2. The microelectrode of embodiment 1, wherein the first surface and the second surface are not parallel.
3. The microelectrode of embodiment 1 or embodiment 2, wherein one or both of the first surface and the second surface are curved.
4. The microelectrode of any one of embodiments 1-3, wherein one or both of the first surface and the second surface are semi-circular or semi-elliptical.
5. The microelectrode of embodiment 1 or embodiment 2, wherein one or both of the first surface and the second surface are rectangular, triangular, or trapezoidal.
6. The microelectrode of embodiment 1 or embodiment 2, wherein the first electrode includes a third surface adjacent to first surface and the electrically insulated surface of the substrate, and wherein the second electrode includes a fourth surface adjacent to first surface.
7. The microelectrode of embodiment 6, wherein the first surface and the third surface form a polyhedron situated on a cross-sectional end of the first electrode.
8. The microelectrode of embodiment 6 or embodiment 7, wherein the second surface and the fourth surface form a polyhedron situated on a cross-sectional end of the second electrode.
9. The microelectrode of embodiment 7, wherein the polyhedron formed on the cross-sectional end of the first electrode forms a triangular prism, a quadrahedron, a pentahedron, a hexahedron, a septaheron, or an octahedron.
10. The microelectrode of embodiment 7 or embodiment 9, wherein the polyhedron formed on the cross-sectional end of the second electrode forms a triangular prism, a quadrahedron, a pentahedron, a hexahedron, a septaheron, or an octahedron.

11. The microelectrode of embodiment 1, wherein the second surface area is substantially parallel to the first surface.
12. The microelectrode of any one of embodiments 1-11, wherein the edge length of one or both of the first surface and the second surface ranges from 0.02% to 75.0% of the diameter of the cell or embryo.
13. The microelectrode of any one of embodiments 1-11, wherein the edge length of one or both of the first surface and the second surface ranges from 100 nm to 9 mm.
14. The microelectrode of any one of embodiments 1-11, wherein the edge length of one or both of the first surface and the second surface ranges from 1 μm to 1 mm.
15. The microelectrode of any one of embodiments 1-11, wherein the edge length of one or both of the first surface and the second surface ranges from 5 μm to 100 μm.
16. The microelectrode of any one of embodiments 1-11, wherein the microelectrode is for electroporation of mammalian embryos and the edge length of one or both of the first surface and the second surface ranges from 100 nm to 160 μm.
17. The microelectrode of any one of embodiments 1-11, wherein the microelectrode is for electroporation of mammalian embryos and the edge length of one or both of the first surface and the second surface ranges from 100 nm to 120 μm.
18. The microelectrode of any one of embodiments 1-11 or embodiment 16, where the predetermined distance ranges from 1 μm to 33 mm.
19. The microelectrode of any one of embodiments 1-11 or embodiment 17, where the predetermined distance ranges from 80 μm to 200 μm.
20. The microelectrode of any one of embodiments 1-11, wherein the microelectrode is for electroporation of insect embryo cells and the edge length of one or both of the first surface and the second surface ranges from 100 nm to 16.5 mm.
21. The microelectrode of any one of embodiments 1-11, wherein the microelectrode is for electroporation of insect embryo cells and the edge length of one or both of the first surface and the second surface ranges from 0.18 mm to 3 mm.
22. The microelectrode of any one of embodiments 1-11 or embodiment 20, where the predetermined distance ranges from 0.09 mm to 33 mm.
23. The microelectrode of any one of embodiments 1-11 or embodiment 21, where the predetermined distance ranges from 0.18 mm to 3.75 mm.
24. The microelectrode of any one of embodiments 1-11, wherein the microelectrode is for electroporation of insect embryo cells and the edge length of one or both of the first surface and the second surface ranges from 0.5 mm to 16.5 mm.
25. The microelectrode of any one of embodiments 1-11, wherein the microelectrode is for electroporation of insect embryo cells and the edge length of one or both of the first surface and the second surface ranges from 100 nm to 16.5 mm.
26. The microelectrode of any one of embodiments 1-11 or embodiment 24, wherein the predetermined distance ranges from 1 μm to 10 μm.
27. The microelectrode of any one of embodiments 1-11 or embodiment 25, wherein the predetermined distance ranges from 0.5 mm to 20.63 mm.
28. The microelectrode of any one of embodiments 1-11, wherein the microelectrode is for electroporation of amphibian embryo cells and the edge length of the substrate of one or both of the first surface and the second surface ranges from 100 nm to 2 mm.
29. The microelectrode of any one of embodiments 1-11, wherein the microelectrode is for electroporation of amphibian embryo cells and the edge length of the substrate of one or both of the first surface and the second surface ranges from 1 mm to 2 mm.
30. The microelectrode of any one of embodiments 1-11 or embodiment 28, where the predetermined distance ranges from 0.5 mm to 4 mm.
31. The microelectrode of any one of embodiments 1-11 or embodiment 29, where the predetermined distance ranges from 1 mm to 2.5 mm.
32. The microelectrode of any one of embodiments 1-11, wherein the microelectrode is for electroporation of fish embryo cells and the edge length of one or both of the first surface and the second surface ranges from 100 nm to 9 mm.
33. The microelectrode of any one of embodiments 1-11, wherein the microelectrode is for electroporation of fish embryo cells and the edge length of one or both of the first surface and the second surface ranges from 0.7 mm to 9 mm.
34. The microelectrode of any one of embodiments 1-11 or embodiment 32, where the predetermined distance ranges from 0.45 mm to 18 mm.
35. The microelectrode of any one of embodiments 1-11 or embodiment 33, where the predetermined distance ranges from 0.7 mm to 11.25 mm.
36. The microelectrode of any one of embodiments 1-11, wherein the microelectrode is for electroporation of plant protoplasts and the edge length of one or both of the first surface and the second surface ranges from 100 nm to 40 μm.
37. The microelectrode of any one of embodiments 1-11, wherein the microelectrode is for electroporation of plant protoplasts and the edge length of one or both of the first surface and the second surface ranges from 10 μm 1 to 40 μm.
38. The microelectrode of any one of embodiments 1-11 or embodiment 36, where the predetermined distance ranges from 5 μm to 80 μm.
39. The microelectrode of any one of embodiments 1-11 or embodiment 37, where the predetermined distance ranges from 10 μm to 50 μm.
40. The microelectrode of embodiment 1, wherein the microelectrode is for electroporation of pollen and the edge length of one or both of the first surface and the second surface ranges from 100 nm to 120 μm.
41. The microelectrode of embodiment 1, wherein the microelectrode is for electroporation of pollen and the edge length of one or both of the first surface and the second surface ranges from 6 μm to 120 μm.
42. The microelectrode of any one of embodiments 1-11 or embodiment 40, where the predetermined distance ranges from 3 μm to 240 μm.
43. The microelectrode of any one of embodiments 1-11 or embodiment 41, where the predetermined distance ranges from 6 μm to 150 μm.
44. The microelectrode of embodiment 1, wherein the microelectrode is for electroporation of fungi protoplast and the edge length of one or both of the first surface and the second surface ranges from 100 nm to 5 μm.

45. The microelectrode of embodiment 1, wherein the microelectrode is for electroporation of fungi protoplast and the edge length of one or both of the first surface and the second surface ranges from 2 μm to 5 μm.
46. The microelectrode of any one of embodiments 1-11 or embodiment 44, where the predetermined distance ranges from 1 μm to 10 μm.
47. The microelectrode of any one of embodiments 1-11 or embodiment 45, where the predetermined distance ranges from 2 μm to 6.5 μm.
48. The microelectrode of any one of embodiments 1-11, wherein the microelectrode is for electroporation of yeast and the edge length of one or both of the first surface and the second surface ranges from 100 nm to 4 μm.
49. The microelectrode of any one of embodiments 1-11, wherein the microelectrode is for electroporation of yeast and the edge length of one or both of the first surface and the second surface ranges from 3 μm to 4 μm.
50. The microelectrode of any one of embodiments 1-11 or embodiment 48, where the predetermined distance ranges from 1.5 μm to 8 μm.
51. The microelectrode of any one of embodiments 1-11 or embodiment 49, where the predetermined distance ranges from 3 μm to 5 μm.
52. The microelectrode of any one of embodiments 1-11, wherein the microelectrode is for electroporation of mammalian immune cells and the edge length of one or both of the first surface and the second surface ranges from 100 nm to 80 μm.
53. The microelectrode of any one of embodiments 1-11, wherein the microelectrode is for electroporation of mammalian immune cells and the edge length of one or both of the first surface and the second surface ranges from 5 μm to 80 μm.
54. The microelectrode of any one of embodiments 1-11 or embodiment 52, where the predetermined distance ranges from 2.5 μm to 160 μm.
55. The microelectrode of any one of embodiments 1-11 or embodiment 53, where the predetermined distance ranges from 5 μm to 100 μm.
56. The microelectrode of any one of embodiments 1-11, wherein the microelectrode is for electroporation of mammalian connective tissue cells and the edge length of one or both of the first surface and the second surface ranges from 100 nm to 20 μm.
57. The microelectrode of any one of embodiments 1-11, wherein the microelectrode is for electroporation of mammalian connective tissue cells and the edge length of one or both of the first surface and the second surface ranges from 2 μm to 20 μm.
58. The microelectrode of any one of embodiments 1-11 or embodiment 56, where the predetermined distance ranges from 1 μm to 40 μm.
59. The microelectrode of any one of embodiments 1-11 or embodiment 57, where the predetermined distance ranges from 2 μm to 25 μm.
60. The microelectrode of any one of embodiments 1-11, wherein the microelectrode is for electroporation of mammalian endothelial cells and the edge length of one or both of the first surface and the second surface ranges from 100 nm to 20 μm.
61. The microelectrode of any one of embodiments 1-11, wherein the microelectrode is for electroporation of mammalian endothelial cells and the edge length of one or both of the first surface and the second surface ranges from 10 μm to 20 μm.
62. The microelectrode of any one of embodiments 1-11 or embodiment 60, where the predetermined distance ranges from 5 μm to 40 μm.
63. The microelectrode of any one of embodiments 1-11 or embodiment 61, where the predetermined distance ranges from 10 μm to 25 μm.
64. The microelectrode of any one of embodiments 1-11, wherein the microelectrode is for electroporation of mammalian epithelial cells and the edge length of one or both of the first surface and the second surface ranges from 100 nm to 120 μm.
65. The microelectrode of any one of embodiments 1-11, wherein the microelectrode is for electroporation of mammalian epithelial cells and the edge length of one or both of the first surface and the second surface ranges from 10 μm to 120 μm.
66. The microelectrode of any one of embodiments 1-11 or embodiment 64, where the predetermined distance ranges from 5 μm to 240 μm.
67. The microelectrode of any one of embodiments 1-11 or embodiment 65, where the predetermined distance ranges from 10 μm to 150 μm.
68. The microelectrode of any one of embodiments 1-11, wherein the microelectrode is for electroporation of mammalian muscle cells and the edge length of the substrate of one or both of the first surface and the second surface ranges from 200 nm to 40 mm.
69. The microelectrode of any one of embodiments 1-11, wherein the microelectrode is for electroporation of mammalian muscle cells and the edge length of the substrate of one or both of the first surface and the second surface ranges from 1 mm to 40 mm.
70. The microelectrode of any one of embodiments 1-11 or embodiment 68, where the predetermined distance ranges from 5 μm to 80 mm.
71. The microelectrode of any one of embodiments 1-11 or embodiment 69, where the predetermined distance ranges from 1 mm to 50 mm.
72. The microelectrode of any one of embodiments 1-11, wherein the microelectrode is for electroporation of mammalian muscle cells and the edge length of the substrate of one or both of the first surface and second surface ranges from 10 μm to 100 μm.
73. The microelectrode of any one of embodiments 1-11 or embodiment 68, where the predetermined distance ranges from 10 μm to 125 mm.
74. The microelectrode of any one of embodiments 1-11, wherein the microelectrode is for electroporation of mammalian mesenchymal stem cells and the edge length of one or both of the first surface and the second surface ranges from 100 nm to 30 μm.
75. The microelectrode of any one of embodiments 1-11, wherein the microelectrode is for electroporation of mammalian mesenchymal stem cells and the edge length of one or both of the first surface and the second surface ranges from 20 μm to 30 μm.
76. The microelectrode of any one of embodiments 1-11 or embodiment 74, where the predetermined distance ranges from 10 μm to 60 μm.
77. The microelectrode of any one of embodiments 1-11 or embodiment 75, where the predetermined distance ranges from 20 μm to 37.5 μm.
78. The microelectrode of embodiment 1, wherein the microelectrode is for electroporation of mammalian embryonic stem cells and the edge length of one or both of the first surface and the second surface ranges from 100 nm to 15 µm.
79. The microelectrode of embodiment 1, wherein the microelectrode is for electroporation of mammalian embryonic stem cells and the edge length of one or both of the first surface and the second surface ranges from 10 µm to 15 µm.
80. The microelectrode of any one of embodiments 1-11 or embodiment 78, where the predetermined distance ranges from 5 µm to 30 µm.
81. The microelectrode of any one of embodiments 1-11 or embodiment 79, where the predetermined distance ranges from 10 µm to 18.75 µm.
82. The microelectrode of any one of embodiments 1-11, wherein the microelectrode is for electroporation of mammalian IPSC cells and the edge length of one or both of the first surface and the second surface ranges from 100 nm to 30 µm.
83. The microelectrode of any one of embodiments 1-11, wherein the microelectrode is for electroporation of mammalian IPSC cells and the edge length of one or both of the first surface and the second surface ranges from 10 µm to 30 µm.
84. The microelectrode of any one of embodiments 1-11 or embodiment 82, where the predetermined distance ranges from 5 µm to 60 µm.
85. The microelectrode of any one of embodiments 1-11 or embodiment 83, where the predetermined distance ranges from 20 µm to 37.5 µm.
86. The microelectrode of any one of embodiments 1-11, wherein the microelectrode is for electroporation of mammalian CHO cells and the edge length of one or both of the first surface and the second surface ranges from 100 nm to 15 µm.
87. The microelectrode of any one of embodiments 1-11, wherein the microelectrode is for electroporation of mammalian CHO cells and the edge length of one or both of the first surface and the second surface ranges from 10 µm to 15 µm.
88. The microelectrode of any one of embodiments 1-11 or embodiment 86, where the predetermined distance ranges from 5 µm to 30 µm.
89. The microelectrode of any one of embodiments 1-11 or embodiment 87, where the predetermined distance ranges from 10 µm to 18.75 µm.
90. The microelectrode of any one of embodiments 1-11, wherein the microelectrode is for electroporation of mammalian HeLA cells and the edge length of one or both of the first surface and the second surface ranges from 100 nm to 20 µm.
91. The microelectrode of any one of embodiments 1-11, wherein the microelectrode is for electroporation of mammalian HeLA cells and the edge length of one or both of the first surface and the second surface ranges from 10 µm to 20 µm.
92. The microelectrode of any one of embodiments 1-11 or embodiment 90, where the predetermined distance ranges from 5 µm to 40 µm.
93. The microelectrode of any one of embodiments 1-11 or embodiment 91, where the predetermined distance ranges from 10 µm to 25 µm.
94. The microelectrode of any one of embodiments 1-11, wherein the microelectrode is for electroporation of mammalian HEK293 cells and the edge length of one or both of the first surface and the second surface ranges from 100 nm to 15 µm.
95. The microelectrode of any one of embodiments 1-11, wherein the microelectrode is for electroporation of mammalian HEK293 cells and the edge length of one or both of the first surface and the second surface ranges from 10 µm to 15 µm.
96. The microelectrode of any one of embodiments 1-11 or embodiment 94, where the predetermined distance ranges from 5 µm to 30 µm.
97. The microelectrode of any one of embodiments 1-11 or embodiment 95, where the predetermined distance ranges from 10 µm to 18.75 µm.
98. The microelectrode of any one of embodiments 1-16 and 94, wherein the predetermined distance ranges from 0.5 times the diameter of the cell to 2.0 times the diameter of the cell or embryo.
99. The microelectrode of any one of embodiments 1-16 and 94, wherein the predetermined distance ranges from 0.75 times the diameter of the cell to 1.5 times the diameter of the cell or embryo.
100. The microelectrode of any one of embodiments 1-98, wherein one or both of the first surface and the second surface are rectangular, triangular, trapezoidal, semicircular, or semi-elliptical.
101. The microelectrode of any one of embodiments 1-100, wherein one or both of the first electrode and the second electrode are deposited on the electrically insulated surface using techniques selected from the group consisting of physical vapor deposition, chemical vapor deposition, electroplating, and/or wet etching.
102. The microelectrode of any one of embodiments 1-101, wherein one or both of the first electrode and the second electrode include a hydrophilic surface coating.
103. The microelectrode of any one of embodiments 1-102, wherein one or both of the first electrode and the second electrode are made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy, graphene, indium tin oxide, tin, ruthenium, ruthenium oxide, rhodium, zirconium, TiNi, Al—Si—Cu, and cobalt.
104. The microelectrode of any one of embodiments 1-103, wherein one or both of the first electrode and the second electrode are made from a conductive alloy.
105. The microelectrode of any one of embodiments 1-104, wherein the channel is configured to isolate the cell or embryo between the first surface and the second surface.
106. The microelectrode of any one of embodiments 1-105, wherein the substrate includes one or more fluidic vents situated within the electrically insulated surface of the substrate between the first surface and the second surface.
107. The microelectrode of any one of embodiments 1-105, wherein the substrate includes one or more fluidic vents situated within a second electrically insulated surface of the substrate between the first surface and the second surface, wherein the second electrically insulated surface of the substrate is orthogonal to both the electrically insulated surface of the substrate and the first surface.
108. The microelectrode of embodiment 106 or embodiment 107, wherein the one or more fluidic vents are smaller than the diameter of the cell or embryo.
109. The microelectrode of any one of embodiments 106-108, wherein the liquid medium flows through the one or more vents and positions the cell or embryo within the channel between the first electrode and the second electrode.

110. The microelectrode of any one of embodiments 1-109, further comprising a second substrate with a second electrically insulated surface situated above the channel, wherein the second electrically insulated surface is substantially parallel to the first electrically insulated surface and is separated from the first electrically insulated surface a second predetermined distance that is 100% to 250%, 50% to 200%, 50% to less than 100%, or 10% to 50% of the diameter of the cell or the embryo to position the cell or embryo within the channel between the first electrode and the second electrode.

111. The microelectrode of any one of embodiments 1-109, further comprising:
a third electrode adjacent to the electrically insulated surface of the substrate; and
a fourth electrode adjacent to the electrically insulated surface of the substrate, wherein the third electrode and the fourth electrode are situated adjacent to the channel or within the channel to accommodate electrical contact between the third electrode and the fourth electrode and the cell or embryo.

112. The microelectrode of embodiment 111, wherein cross-sections of one or both of the third electrode and the fourth electrode are rectangular, triangular, trapezoidal, semi-circular, or semi-elliptical.

113. The microelectrode of embodiment 111 or embodiment 112, wherein an edge length of one or both of the third electrode and the fourth electrode is less than the edge length of the first surface or the second surface.

114. The microelectrode of any one of embodiments 111-113, wherein an edge length of one or both of the third electrode and the fourth electrode ranges from 100 nm to 3.3 µm.

115. The microelectrode of any one of embodiments 111-114, wherein one or both of the third electrode and the fourth electrode include a hydrophilic surface coating.

116. The microelectrode of any one of embodiments 111-115, wherein one or both of the third electrode and the fourth electrode are made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy (NiFe), graphene, indium tin oxide, tin, ruthenium, ruthenium oxide, rhodium, zirconium, TiNi, Al—Si—Cu, and cobalt.

117. The microelectrode of any one of embodiments 111-116, wherein one or both of the third electrode and the fourth electrode are made from a conductive alloy.

118. The microelectrode of any one of embodiments 1-114, wherein the liquid medium includes a polynucleotide with a concentration ranging between 1 ng/µL to 10 mg/µL.

119. The microelectrode of any one of embodiments 1-114, wherein the liquid medium includes a polynucleotide with a concentration ranging between 1 ng/µL to 10 µg/µL.

120. The microelectrode of embodiment 118, wherein the polynucleotide is a polyribonucleotide.

121. The microelectrode of embodiment 120, wherein the polyribonucleotide is in a complex with a polypeptide.

122. The microelectrode of embodiment 120, wherein the polyribonucleotide is in a polypeptide.

123. The microelectrode of any one of embodiments 1-118, wherein the substrate is glass or silicon.

124. The microelectrode of embodiment 123, wherein the glass is selected from the group consisting of Pyrex 7740, BK7 glass, Borofloat 33, Corning Eagle glass, D263, Gorilla glass, and soda-lime glass.

125. The microelectrode of any one of embodiments 1-121, wherein the substrate is fused silica quartz or single crystal quartz.

126. The microelectrode of any one of embodiments 1-121, wherein the substrate is silicon-on-insulator.

127. The microelectrode of embodiment 126, wherein the silicon-on-insulator is selected from the group consisting of silicon nitride on silicon and silicon-oxide on silicon.

128. The microelectrode of any one of embodiments 1-121, wherein the substrate is germanium or germanium-on-insulator.

129. The microelectrode of any one of embodiments 1-121, wherein the substrate is zinc oxide.

130. The microelectrode of any one of embodiments 1-121, wherein the substrate is a polymer.

131. The microelectrode of embodiment 130, wherein the polymer is selected from the group consisting of Cast acrylic, ABS, nylon, polyethylene, cyclic olefin copolymer and polymer, acetal, polycarbonate, PETG, polyimide, FEP, PTFE, Polystyrene, polypropylene, silicone, PVC, polyurethane, PMMA, and PDMS.

132. The microelectrode of any one of embodiments 1-121, wherein the substrate is polydimethylsiloxane.

133. The microelectrode of any one of embodiments 1-121, wherein the substrate is low-temperature co-fired ceramic.

134. The microelectrode of any one of embodiments 1-121, wherein the substrate is a positive or negative photoresist.

135. A microfluidic chip for electroporation of multiple individual cells or embryos, comprising two or more of the microelectrodes of any one of embodiments 1-123, wherein at least two of the two or more of the microelectrodes are fluidly coupled by a transport channel.

136. A microfluidic array for electroporation of multiple individual cells or embryos, comprising two or more of the microelectrodes of any one of embodiments 1-123.

137. An electroporation system comprising:
a microelectrode of any one of embodiments 1-123; and
a first signal generator electrically coupled to the first electrode and the second electrode, wherein the first signal generator is configured to generate a signal between the first electrode and the second electrode that induces a uniform electric field with substantially parallel electric field lines between the first surface and the second surface, and wherein a sensing signal is received by either the first electrode or the second electrode.

138. The electroporation system of embodiment 137, wherein the generated signal is a sinusoid waveform or a non-sinusoidal waveform.

139. The electroporation system of embodiment 138, wherein the non-sinusoidal waveform is an exponential waveform, a square waveform, a triangular waveform, or a saw-tooth waveform.

140. The system of any one of embodiments 137-139, wherein the generated signal has a frequency between 1 Hz to 100 GHz.
141. The system of any one of embodiments 137-139, wherein the generated signal has a frequency between 1 Hz to 1 kHz 100 GHz.
142. The system of any one of embodiments 137-140, wherein the generated signal has a duty cycle of 50%.
143. The electroporation system of any one of embodiments 137-140, wherein the induced electric field ranges between 10 V/cm to 5 kV/cm.
144. The electroporation system of any one of embodiments 137-140, wherein the induced electric field ranges between 100 V/cm to 4 kV/cm.
145. The electroporation system of any one of embodiments 137-143, further comprising:
a switch electrically coupled to the first electrode and the second electrode, wherein the switch is configured to suppress an electric field between the first surface and the second surface in a first mode and provide an electric field between the first surface and the second surface in a second mode.
146. The electroporation system of embodiment 145, wherein the switch is configured to toggle between the first mode and the second mode at predetermined periodicity.
147. The electroporation system of embodiment 146, wherein the predetermined periodicity ranges from 100 µs to 50 ms.
148. The electroporation system of embodiment 145, wherein the switch includes a bi-directional multiplexer coupled to a microcontroller or a computer.
149. The electroporation system of embodiment 145, wherein the switch is a switching circuit.
150. The electroporation system of embodiment 149, wherein the switching circuit includes the first signal generator to form a mono-stable multi-vibrator.
151. The electroporation system any one of embodiments 137-147, further comprising:
a second signal generator electrically coupled to the third electrode and the fourth electrode, wherein the second signal generator is configured to inject a signal at any of the first, second, third, or fourth electrodes.
152. The electroporation system of embodiment 151, further comprising:
a signal extractor electrically coupled to the fourth electrode, wherein the signal extractor is configured to capture a signal response from the injected signal at any of the first, second, third, or fourth electrodes.
153. The electroporation system of embodiment 152, wherein the signal response at the fourth electrode in relation to the injected signal at any of the first, second, third, or fourth electrodes is proportional to the impedance of the cell or embryo.
154. The electroporation system of embodiment 152, wherein the signal extractor is an analog-to-digital converter.
155. The electroporation system of embodiment 152, wherein the signal extractor is a potentiostat or a galvanostat.
156. The electroporation system of embodiment 152, wherein the signal extractor is a differential impedance matching network.
157. The electroporation system of embodiment 152, wherein the signal extractor is an AC coupled bridge network.
158. The electroporation system of embodiment 152, wherein the signal extractor is an auto-balancing bridge network.
159. A method, comprising:
configuring the microelectrode of any one of embodiments 1-134;
determining a permeability threshold, wherein the permeability threshold corresponds to a minimum amount of electrical energy applied to the cell or embryo at which cell membrane permeability is detected;
applying a signal between the first electrode and the second electrode at the permeability threshold;
injecting, at a third electrode, a signal,
extracting, at a fourth electrode, a response to the injected signal, wherein the cell or embryo is electrically coupled between the third electrode and the fourth electrode; and
storing the signal response in a non-transitory computer readable-medium.
160. The method of embodiment 159, further comprises: conditioning the extracted signal response.
161. The method of embodiment 160, wherein the conditioning includes one or more low pass filters.
162. The method of embodiment 160 or embodiment 161, wherein the conditioning includes amplifying the extracted signal response.
163. The method of any one of embodiments 159-162, wherein the injected signal includes one or more frequencies.
164. The method of any one of embodiments 159-163, wherein determining the permeability threshold comprises:
applying a first test signal between the first electrode and the second electrode at a predetermined electrical energy level;
injecting, at the third electrode, a second test signal while the first test signal is being applied;
extracting, at the fourth electrode, a response to the second test signal;
determining whether the response to the second test signal is characteristic of membrane permeability of the cell or embryo; and
in accordance with a determination that the response to the second test signal is characteristic of membrane permeability of the cell or embryo, storing electrical parameters associated with the predetermined electrical energy level.
165. The method of embodiment 164 further comprises: conditioning the extracted second test signal response.
166. The method of embodiment 165, wherein the conditioning includes one or more low pass filters.
167. The method of embodiment 164 or embodiment 165, wherein the conditioning includes amplifying the extracted signal response.
168. The method of any one of embodiments 164-167, wherein determining the permeability threshold further comprises:
in accordance with a determination that the response to the second test signal is uncharacteristic of membrane permeability of the cell or embryo:
iteratively adjusting the predetermined electrical energy level of the signal between the first electrode and the second electrode until a determination that the response to the second test signal is characteristic of membrane permeability of the cell or embryo; and storing electrical parameters associated with the adjusted predetermined electrical energy level.

BRIEF DESCRIPTION OF THE FIGURES

For a better understanding of the various described examples, reference should be made to the description below, in conjunction with the following figures in which like reference numerals refer to corresponding parts throughout the figures.

DETAILED DESCRIPTION

Figure 1A:
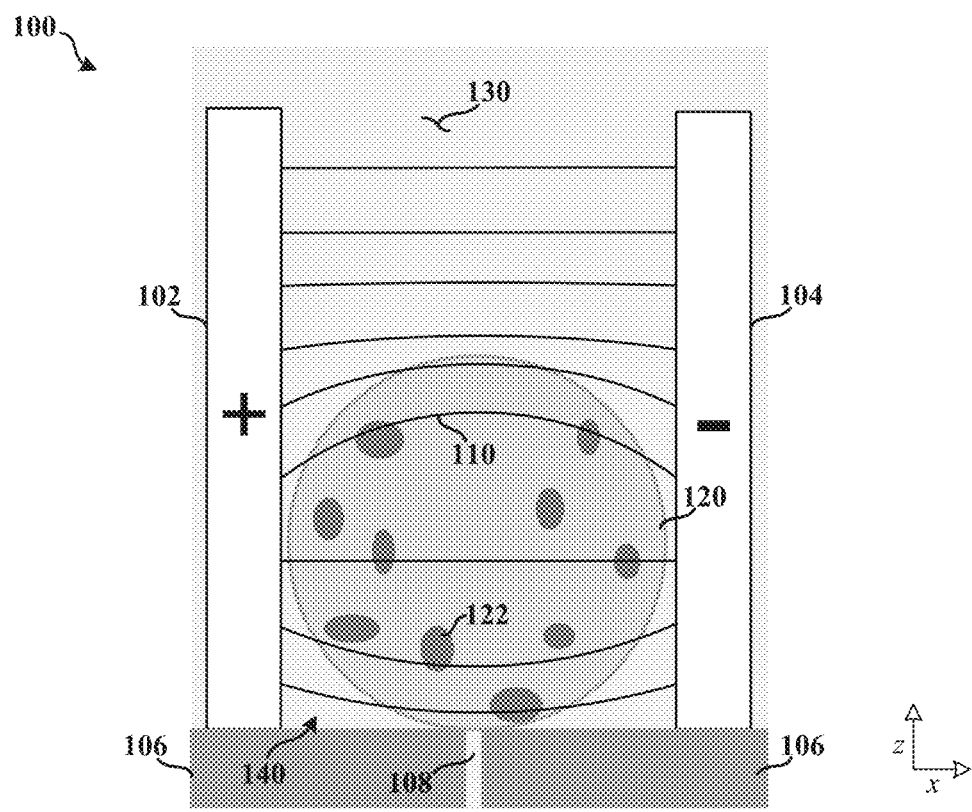
FIG. 1A illustrates an exemplary microelectrode probe with electroporation electrodes.

The detailed description set forth below in connection with the appended drawings is intended as a description of various configurations and is not intended to represent the only configurations in which the concepts described herein can be practiced. The detailed description includes specific details for the purpose of providing a thorough understanding of various concepts. However, it will be apparent to those skilled in the art that these concepts can be practiced without these specific details. In some instances, well-known structures and components are shown in block diagram form in order to avoid obscuring such concepts.

Examples of a microelectrode probe, microelectrode probe array, and microelectrode probe system for electroporation will now be presented with reference to various electronic devices and methods. These electronic devices and methods will be described in the following detailed description and illustrated in the accompanying drawing by various blocks, components, circuits, steps, processes, algorithms, etc. (collectively referred to as "elements"). These elements can be implemented using electronic hardware, computer software, or any combination thereof. Whether such elements are implemented as hardware or software depends upon the particular application and design constraints imposed on the overall system.

By way of example, an element, or any portion of an element, or any combination of elements of the various electronic devices of the electroporation system can be implemented using one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionalities described throughout this disclosure. One or more processors in the processing system can execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more examples, the functions described for the electroporation system can be implemented in hardware, software, or any combination thereof. If implemented in software, the functions can be stored on or encoded as one or more instructions or code on a computer-readable medium. Computer-readable media can include transitory or non-transitory computer storage media for carrying or having computer-executable instructions or data structures stored thereon. Both transitory and non-transitory storage media can be any available media that can be accessed by a computer as part of the processing system. By way of example, and not limitation, such computer-readable media can include a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer-executable code in the form of instructions or data structures accessible by a computer. Further, when information is transferred or provided over a network or another communications connection (either hardwired, wireless, or combination thereof) to a computer, the computer or processing system properly determines the connection as a transitory or non-transitory computer-readable medium, depending on the particular medium. Thus, any such connection is properly termed a computer-readable medium. Combinations of the above should also be included within the scope of the computer-readable media. Non-transitory computer-readable media exclude signals per se and the air interface.

The present disclosure describes a microelectrode probe that traps a cell or embryo between electroporation electrodes. The microelectrode probe includes electroporation electrodes that are shorter than the diameter of the cell or embryo and are separated from each other at a predetermined distance. This predetermined distance may be strictly greater than the diameter of the cell or embryo so that the cell or embryo may fit between the electrodes. Alternatively, the predetermined distance may be 50% to 200% of the diameter of the cell or embryo; predetermined distances less than 100% of the diameter squeezes the cell or embryo into the trap, which has the benefit of holding the cell or embryo in a fixed position throughout the process. During electroporation a voltage (e.g., pulse or signal) is applied to the electroporation electrodes to produce a uniform electric field between the electroporation electrodes, which induces pore formation across the membrane of the cell or embryo. Electroporation techniques that use electroporation electrodes shorter than the diameter of the cell or embryo unexpectedly increased the amount of electric field strength that a cell or embryo can safely withstand before suffering permanent damage. Elevated electric field strengths induce larger pores on the membrane of the cell or embryo and the ability of a microelectrode probe to safely induce larger pore formation facilitates therapies that deliver large molecules into cells or embryos. To illustrate this phenomenon, Table 1 below shows side-by-side comparisons between the disclosed method ("Ravata") and the standard method ("Normal EP") for eight unique Clustered Regularly Interspaced Short Palindromic Repeats (CRISPR) gene-knockouts. The results indicate that embryos used with a microelectrode array described herein were safely exposed to the same electric field for two-and-a-half to five times as long as they were with Normal EP without loss in survival rates and with an increase in gene-editing efficiency. Performing Normal EP at higher durations than 18 ms, the survival rate of embryos significantly plummeted almost immediately.

TABLE 1

| Electric Field [V/cm] | Ravata Total Embryo Field Duration [ms] | Normal EP Total Field Duration [ms] | Ravata Outcome (0 = Fail, 1 = Success) | Normal EP Outcome (0 = Fail, 1 = Success) |
| --- | --- | --- | --- | --- |
| 300 | 45 | 18 | 1 | 1 |
| 300 | 90 | 18 | 1 | 0 |
| 300 | 90 | 18 | 1 | 0 |
| 300 | 45 | 18 | 1 | 1 |
| 300 | 45 | 18 | 1 | 0 |
| 300 | 90 | 18 | 1 | 0 |
| 300 | 90 | 18 | 0 | 0 |
| 300 | 90 | 18 | 1 | 1 |

FIG. 1A illustrates an exemplary microelectrode probe 100 with electroporation electrodes. As depicted in FIG. 1A, a first electroporation electrode 102 and a second electroporation electrode 104 are situated on a substrate 106. The substrate 106 has an electrically insulated surface that prevents the first electroporation electrode 102 from electrically shorting with the second electroporation electrode 104. In some examples, the substrate 106 is glass or silicon. In some instances, the glass is selected from the group consisting of Pyrex 7740, BK7 glass, Borofloat 33, Corning Eagle glass, D263, Gorilla glass, and soda-lime glass. In some examples, the substrate 106 is fused silica quartz or single crystal quartz. In some examples, the substrate 106 is silicon-on-insulator (SOI). In some instances, the silicon-on-insulator (SOI) is selected from the group consisting of silicon nitride on silicon and silicon-oxide on silicon. In some examples, the substrate 106 is germanium or germanium-on-insulator. In some examples, the substrate 106 is zinc oxide. In some examples, the substrate 106 is a polymer. In some instances, the polymer is selected from the group consisting of Cast acrylic, ABS, nylon, polyethylene, cyclic olefin copolymer and polymer, acetal, polycarbonate, PETG, polyimide, FEP, PTFE, Polystyrene, polypropylene, silicone, PVC, polyurethane, PMMA, and PDMS. In some examples, the substrate 106 is polydimethylsiloxane. In some examples, the substrate 106 is a low-temperature co-fired ceramic. In some examples, the substrate 106 is a positive or negative photoresist.

The first electroporation electrode 102 and the second electroporation electrode 104 each have a surface that is substantially orthogonal to the electrically insulated surface (e.g., on the x-y plane) of the substrate 106. In some examples, one or both of the first electroporation electrode 102 and the second electroporation electrode 104 are deposited on the electrically insulated surface using techniques such as physical vapor deposition, chemical vapor deposition, electroplating, and/or wet etching. In some examples, one or both of the first electroporation electrode 102 and the second electroporation electrode 104 may be deposited; deposited then grown; deposited then etched; or deposited then grown then etched on the insulated surface. In some examples, one or both of the first electroporation electrode 102 and the second electroporation electrode 104 include a hydrophilic surface coating. In some examples, one or both of the first electroporation electrode 102 and the second electroporation electrode 104 are made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy, graphene, indium tin oxide, tin, ruthenium, ruthenium oxide, rhodium, zirconium, TiNi, Al—Si—Cu, and cobalt. In some examples, one or both of the first electroporation electrode 102 and the second electroporation electrode 104 are made from a conductive alloy.

The second electroporation electrode 104 is separated from the first electroporation electrode 102 at the surface that is substantially orthogonal to the electrically insulated surface (e.g., on the x-y plane) of the substrate 106 a predetermined distance so as to form a channel 140. In general, the channel 140 is configured to isolate the cell or embryo 120 between the one or both surfaces (e.g., the first surface and the second surface) of the first electroporation electrode 102 and the second electroporation electrode 104 that are substantially orthogonal to the electrically insulated surface (e.g., on the x-y plane) of the substrate 106. In some examples, the predetermined distance between the first electroporation electrode 102 and the second electroporation electrode 104 is larger than the diameter of cell or embryo 120. In some examples, the predetermined distance between the first electroporation electrode 102 and the second electroporation electrode 104 is 50% to 200%, 50% to less than 100%, or even 10% to 50% of the diameter of the cell or embryo. In some examples, the one or both surfaces (e.g., the first surface and the second surface) of the first electroporation electrode 102 and the second electroporation electrode 104 that are substantially orthogonal to the electrically insulated surface (e.g., on the x-y plane) of the substrate 106 are rectangular, triangular, trapezoidal, semicircular, or semi-elliptical.

As depicted in FIG. 1A, the substrate 106 includes a fluidic vent 108 situated within the electrically insulated surface (e.g., on the x-y plane) of the substrate 106 between the first electroporation electrode 102 and the second electroporation electrode 104. The vent 108 facilitates positioning of the cell or embryo 120 within the channel 140 as a liquid medium 130 situated within the channel 140 can flow through the vent 108 so as to draw the cell or embryo 120 towards the channel 140. The vent 108 further facilitates a suction to the cell or embryo 120 once positioned (e.g., in contact with the electrically insulated surface (e.g., on the x-y plane) of the substrate 106). In general, the substrate 106 includes one or more fluidic vents 108 situated within the electrically insulated surface (e.g., on the x-y plane) of the substrate 106 between the one or both surfaces (e.g., the first surface and the second surface) of the first electroporation electrode 102 and the second electroporation electrode 104 that are substantially orthogonal to the electrically insulated surface (e.g., on the x-y plane) of the substrate 106.

It should be appreciated that the liquid medium 130 is capable of fluidic transport of the cell or embryo 120 through or into the channel. In some examples, the liquid medium 130 includes a polynucleotide with a concentration ranging between 1 ng/µL to 10 µg/µL. In some examples, the polynucleotide concentration ranges between 1 ng/µL to 10 mg/µL, preferably between 1 ng/µL to 100 µg/µL or, for higher efficiency, between 100 µg/µL to 1 mg/µL. The concentration of CRISPR RNP (ribonucleic protein or pre-complexed Cas9) used for both electroporation methods performed to produce Tables 1 and 2 was 10 µg/µL. In some instances, the polynucleotide is a polyribonucleotide. In some instances, the polyribonucleotide is in a complex with a polypeptide. In some instances, the polyribonucleotide is in a non-complex with a polypeptide. In addition, it should be appreciated that the liquid medium 130 is capable of supporting an electric field and therefore does not electrically short the first electroporation electrode 102 to the second electroporation electrode 104.

In the configuration depicted in FIG. 1A, an edge length of each of the substantially orthogonal surface of the first electroporation electrode 102 and the second electroporation electrode 104 that extends in a direction (e.g., positive z-direction) orthogonal to the electrically insulated surface (e.g., on the x-y plane) of the substrate 106 is greater than a diameter of the cell or embryo 120. In this configuration, a voltage potential applied across the first electroporation electrode 102 and the second electroporation electrode 104 induces a uniform electric field with electric field lines 110. As depicted in FIG. 1A, the electric field lines 110 in the liquid medium 130 are relatively orthogonal to the substantially orthogonal surfaces of the first electroporation electrode 102 and the second electroporation electrode 104. As the field lines 110 approach the cell or embryo 120, the electric field lines 110 are perturbed so as to arc in a direction conducive to the change in permittivity between the cell or embryo 120 (e.g., $\varepsilon_{cell/embryo}$) and the liquid medium 130 (e.g., $\varepsilon_{liquid}$). Consequently, the electric field lines 110 remain uniform albeit slightly contouring across the cell or embryo 120.

As depicted in FIG. 1A, the entire cell or embryo 120 is enveloped in the relatively uniform electric field since the edge length of each of the substantially orthogonal surfaces of the first electroporation electrode 102 and the second electroporation electrode 104 that extends in a direction (e.g., positive z-direction) orthogonal to the electrically insulated surface (e.g., on the x-y plane) of the substrate 106 is greater than a diameter of the cell or embryo 120. This means that the applied electric field induces pore 122 formation of the membrane across the entire cell or embryo 120. As such, the number of induced pores 122 across the membrane of the cell or embryo 120 is independent of the position of the cell or embryo with respect to the electrodes (e.g., first electroporation electrode 102 and the second electroporation electrode 104).

Figure 1B:
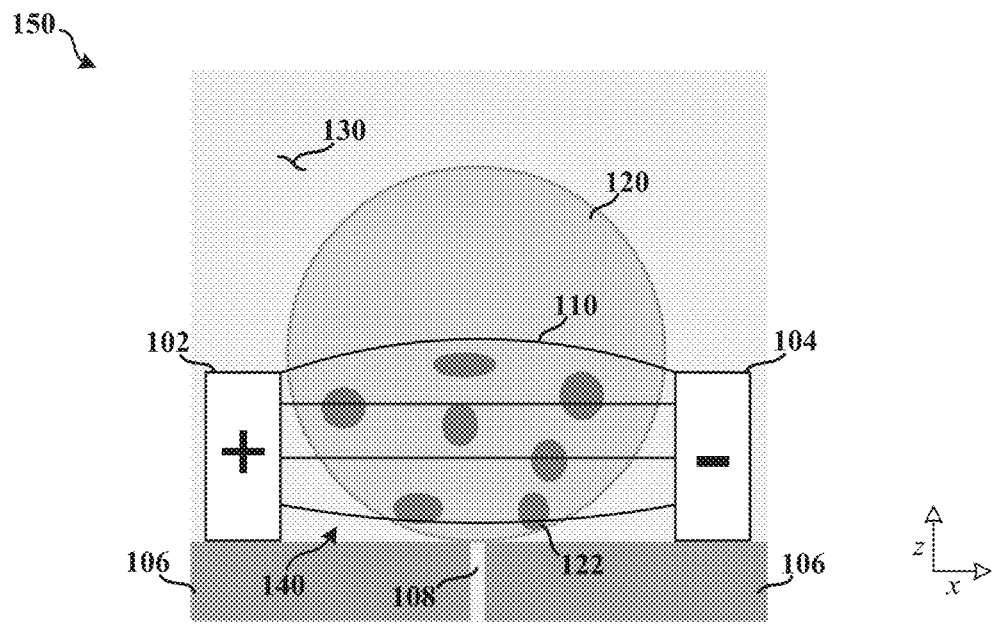
FIG. 1B illustrates an exemplary microelectrode probe with height-reduced electroporation electrodes.

The configuration in FIG. 1A creates pores on the entire membrane and thus has a lower threshold for cell survival than the configuration in FIG. 1B which concentrates pores to a specific region of the cell's membrane. The reason is that the number of adjacent pores 122 in FIG. 1A of the membrane that rupture to form larger and larger pores 122 spans across the entire cell or membrane, which exceeds what the cell or embryo 120 is capable of repairing. Table 2 below lists the results of experiments showcasing the effect of greater electric fields and longer durations.

TABLE 2

| Ravata Electric Field [V/cm] | Ravata Total Field Duration [ms] | Normal EP Electric Field [V/cm] | Normal EP Total Field Duration [ms] | Ravata Viability Outcome [0 or 1] | Normal EP Viability Outcome [0 or 1] |
|---|---|---|---|---|---|
| 350 | 60 | 300 | 18 | 0 | 1 |
| 350 | 60 | 300 | 18 | 1 | 1 |
| 400 | 63 | 300 | 18 | 1 | 1 |
| 435 | 105 | 300 | 18 | 1 | 0 |

FIG. 1B illustrates an exemplary microelectrode probe 150 with height-reduced electroporation electrodes. As depicted in FIG. 1B, a first electroporation electrode 102 and a second electroporation electrode 104 are situated on a substrate 106. The substrate 106 has an electrically insulated surface that prevents the first electroporation electrode 102 from electrically shorting with the second electroporation electrode 104.

The first electroporation electrode 102 and the second electroporation electrode 104 each have a surface that is substantially orthogonal to the electrically insulated surface (e.g., on the x-y plane) of the substrate 106. The second electroporation electrode 104 is separated from the first electroporation electrode 102 at a predetermined distance so as to form a channel 140. In some examples, the predetermined distance between the first electroporation electrode 102 and the second electroporation electrode 104 is larger than the diameter of cell or embryo 120. In some examples, the predetermined distance between the first electroporation electrode 102 and the second electroporation electrode 104 is 50% to 200% of the diameter of the cell or embryo.

As depicted in FIG. 1B, the substrate 106 includes a fluidic vent 108 situated within the electrically insulated surface (e.g., on the x-y plane) of the substrate 106 between the substantially orthogonal surfaces of the first electroporation electrode 102 and the second electroporation electrode 104. The vent 108 facilitates positioning of the cell or embryo within the channel 140 as a liquid medium 130 situated within the channel 140 can flow through the vent so as to draw the cell or embryo 120 towards the channel 140. The vent 108 further facilitates a suction to the cell or embryo 120 once positioned (e.g., in contact with the electrically insulated surface (e.g., on the x-y plane) of the substrate 106). It should be appreciated that the liquid medium 130 is capable of fluidic transport of the cell or embryo 120 through or into the channel. In some examples, the liquid medium 130 includes a polynucleotide with a concentration ranging between 1 ng/µL to 10 µg/µL. In some examples, the polynucleotide concentration ranges between 1 ng/µL to 10 mg/µL, preferably between 1 ng/µL to 100 µg/µL or, for higher efficiency, between 100 µg/µL to 1 mg/µL. In some instances, the polynucleotide is a polyribonucleotide. In some instances, the polyribonucleotide is in a complex with a polypeptide. In some instances, the polyribonucleotide is in a polypeptide. It should also be appreciated that the liquid medium 130 is capable of supporting an electric field and therefore does not electrically short the first electroporation electrode 102 to the second electroporation electrode 104.

In the configuration depicted in FIG. 1B, an edge length of each of the substantially orthogonal surfaces of the first electroporation electrode 102 and the second electroporation electrode 104 that extends in a direction (e.g., positive z-direction) orthogonal to the electrically insulated surface (e.g., on the x-y plane) of the substrate 106 is less than or equal to a diameter of the cell or embryo 120. In this configuration, a voltage potential applied across the first electroporation electrode 102 and the second electroporation electrode 104 induces a relatively uniform electric field with electric field lines 110 within the cell or embryo 120. As depicted in FIG. 1B, the electric field lines 110 are perturbed slightly so as to arc in a direction conducive to the change in permittivity between the cell or embryo 120 (e.g., $\varepsilon_{cell/embryo}$) and the liquid medium 130 (e.g., $\varepsilon_{liquid}$).

As depicted in FIG. 1B, only a portion of the cell or embryo 120 is subjected to the relatively uniform electric field. As such, the applied electric field induces pore 122 formation of the membrane and concentrates it to a portion of the cell or embryo 120. As such, the number of induced pores 122 across the membrane of the cell or embryo 120 correlates with both the position of the cell or embryo 120 with respect to the electrodes (e.g., first electroporation electrode 102 and the second electroporation electrode 104) and the strength of the electric field (e.g., concentration of electric field lines 110).

The induced pores 122 span only a portion of the cell or embryo 120. As such, there remain different portions of the cell or embryo 120 that are undamaged upon completion of electroporation. This means that after electroporation, the cell or embryo 120 can forgo repairing the portion not subject to the electric field and instead focus on repairing the portion subjected to electroporation. The tests shown in Tables 1 and 2 indicate that the cell or embryo 120 can withstand larger induced pores 122 under electroporation for the induced pores 122 that span only a portion of the membrane of the cell or embryo 120 compared to induced pores 122 that span the entire membrane of the cell or embryo 120.

Tests revealed that the administration of an electric field strength greater than o325 V/cm for 18 ms total, or for total durations greater than 18 ms at 300V/cm, is fatal to embryos using the configuration similar to that depicted in FIG. 1A. Surprisingly, under the same condition but adapting the configuration to resemble FIG. 1B (e.g., only reducing edge lengths of each of the substantially orthogonal surfaces of the first electroporation electrode 102 and the second electroporation electrode 104 that extends in a direction (e.g., positive z-direction) orthogonal to the electrically insulated surface (e.g., on the x-y plane) of the substrate 106 to 20 µm), embryos showed a survival rate of 66%. The tests were conducted for embryos that were 80 µm in diameter and subjected to an electric field of 600V/cm for 5 ms, 10 ms, 15 ms, and 20 ms. The tests indicate that localized electric fields provided over a portion of the cell or embryo 120, as depicted in FIG. 1B, induce pore formation only over part of the cell or embryo, thereby providing for the cell or embryo 120 to withstand larger electric fields and to recover from large pore formation. By comparison, tests have experimentally determined that a cell or embryo 120 subject to an electric field using the configuration depicted in FIG. 1B can safely withstand up to ten times (e.g., 10×) the power (via either electric field strength or pulse duration) than a cell or embryo 120 subject to an electric field using the configuration depicted in FIG. 1A. This equates to an increased efficiency of reagent uptake as well as increased survival rates of cells undergoing electroporation.

In later tests conducted with the configuration in FIG. 1B, electric fields greater than or equal to 300 V/cm for total durations greater than five times as long were safely applied to embryos. This led to more efficiency in embryo gene-editing and thus a greater net number of genetically modified embryos. The tests were conducted for embryos approximately 80 µm in diameter and each experiment was designed to knock out a unique gene via an exon-deletion (removal of 600 bp to 800 bp of a gene) mediated by CRISPR Cas9.

Figure 2A:
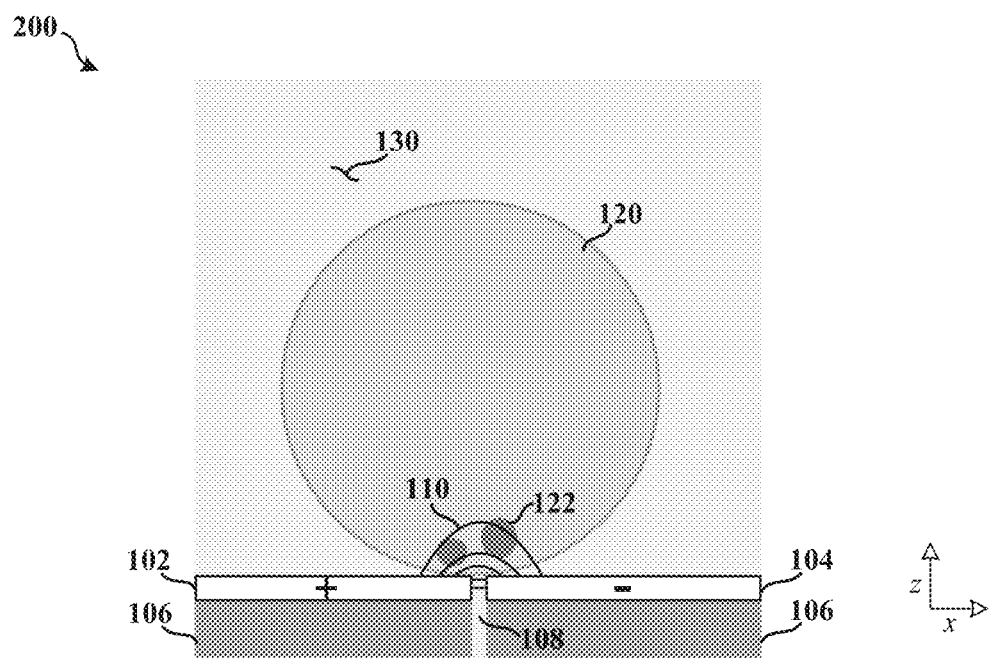
FIG. 2A illustrates an exemplary microelectrode probe with planar electroporation electrodes situated on a substrate.

FIG. 2A illustrates an exemplary microelectrode probe 200 with planar electroporation electrodes situated on a substrate. As depicted in FIG. 2A, a first electroporation electrode 102 and a second electroporation electrode 104 are situated on substrate 106 and are planar with each other. The substrate 106 has an electrically insulated surface that prevents the first electroporation electrode 102 from electrically shorting with the second electroporation electrode 104. Likewise, in some examples, the first electroporation electrode 102 and a second electroporation electrode 104 both have an electrically insulated surface that prevents the possibility that contact with a cell or embryo 120 from electrically shorting first electroporation electrode 102 with the second electroporation electrode 104. In some examples, one or both of the first electroporation electrode 102 and a second electroporation electrode 104 lack an electrically insulated surface.

The substrate 106 includes a fluidic vent 108 situated within the electrically insulated surface (e.g., on the x-y plane) of the substrate 106. The fluidic vent 108 separates the first electroporation electrode 102 from the second electroporation electrode 104. The vent 108 facilitates positioning of the cell or embryo as a liquid medium 130 can flow through the vent 108 so as to draw the cell or embryo 120 onto the first electroporation electrode 102 and the second electroporation electrode 104. The vent 108 also facilitates suction to the cell or embryo 120 once positioned (e.g., in contact with the first electroporation electrode 102 and the second electroporation electrode 104). It should be appreciated that the liquid medium 130 is capable of fluidic transport of the cell or embryo 120 and the liquid medium 130 is capable of supporting an electric field. As such, the liquid medium 130 does not electrically short the first electroporation electrode 102 to the second electroporation electrode 104.

In the configuration depicted in FIG. 2A, a voltage potential applied across the first electroporation electrode 102 and the second electroporation electrode 104 induces a strong electric field in the vent 108 that diminishes in the distance orthogonal to the plane of the substrate 106. More specifically, the intensity of the electric field diminishes in an orthogonal direction (e.g., positive z-direction) from substrate 106 in proportion to the inverse square of the distance from vent 108. As such, the electric field varies based on the position of the cell or embryo 120 and is non-uniform. This positional dependency on a non-uniform field is susceptible to small deviations of the position of the cell or embryo 120 with respect to the first electroporation electrode 102 and the second electroporation electrode 104. This susceptibility can result in large changes to the position and efficiency of pore formation and makes reliable permeabilization difficult. Consequently, the membrane permeabilization is non-symmetrical and the reagent delivery is not as consistent as FIG. 1A or FIG. 1B.

Figure 2B:
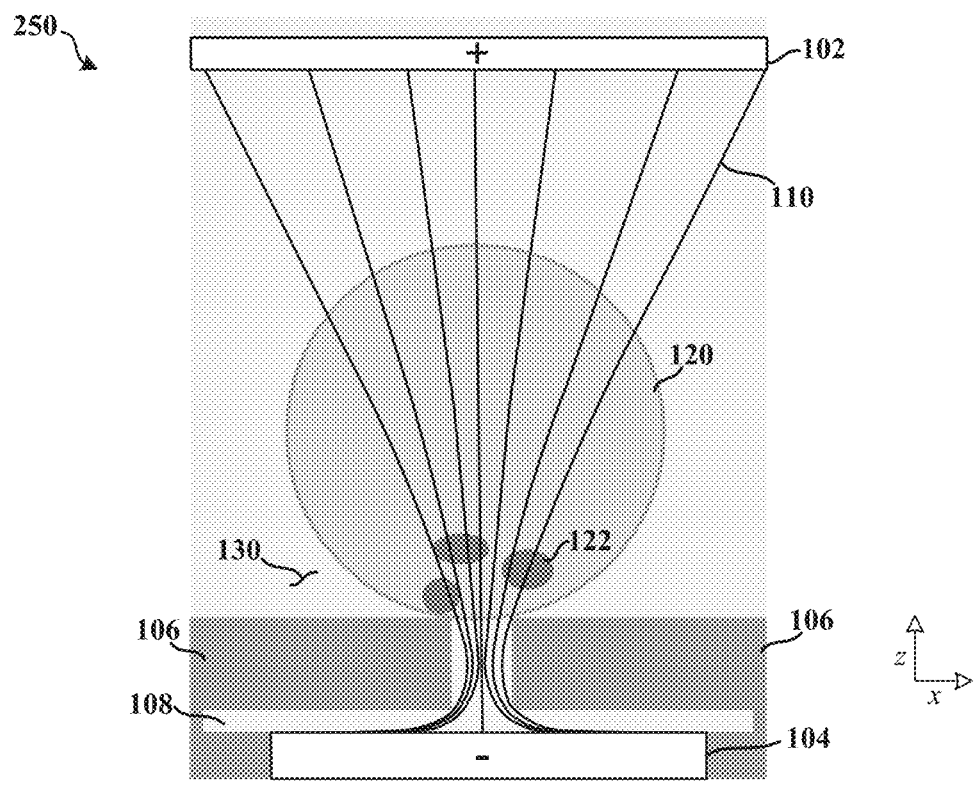
FIG. 2B illustrates an exemplary microelectrode probe with a portion of the substrate situated between electroporation electrodes.

FIG. 2B illustrates an exemplary microelectrode probe 250 with a portion of the substrate situated between electroporation electrodes. As depicted in FIG. 2B, a first electroporation electrode 102 and a second electroporation electrode 104 are parallel to a surface of a substrate 106. The first electroporation electrode 102 is situated a predetermined distance from a substrate 106 in a first direction (e.g., positive z-direction) orthogonal to a surface (e.g., on the x-y plane) of the substrate 106 and the second electroporation electrode 104 is situated a predetermined distance from a substrate 106 in a second direction (e.g., negative z-direction) orthogonal to a surface (e.g., on the x-y plane) of the substrate 106. The second direction (e.g., negative z-direction) is opposite the first direction (e.g., positive z-direction).

A portion of the substrate 106 is interposed between the first electroporation electrode 102 and the second electroporation electrode 104. The portion of the substrate 106 has an electrically insulated surface that prevents the first electroporation electrode 102 from electrically shorting with the substrate 106. The substrate 106 includes a fluidic vent 108 situated between the first electroporation electrode 102 and the second electroporation electrode 104 that bisects the portion of the substrate 106 that is interposed between the first electroporation electrode 102 and the second electroporation electrode 104.

The vent 108 facilitates positioning of the cell or embryo as a liquid medium 130 can flow through the vent 108 so as to draw the cell or embryo 120 between the first electroporation electrode 102 and the second electroporation electrode 104. The vent 108 also facilitates suction to the cell or embryo 120 once positioned (e.g., in contact with the portion of the substrate 106 that is interposed between the first electroporation electrode 102 and the second electroporation electrode 104). It should be appreciated that the liquid medium 130 is capable of fluidic transport of the cell or embryo 120 and the liquid medium 130 is capable of supporting an electric field. As such, the liquid medium 130 does not electrically short the first electroporation electrode 102 to the second electroporation electrode 104.

In the configuration depicted in FIG. 2B, a voltage potential applied across the first electroporation electrode 102 and the second electroporation electrode 104 induces an electric field primarily confined to the vent 108. This is due to the difference in permittivity of the liquid medium 130 (e.g., $\varepsilon_{liquid}$) from the permittivity of the substrate 106 (e.g., $\varepsilon_{substrate}$). As such, the electric field is concentrated along a choke point of the vent 108 where the cell or embryo 120 is suctioned in position. Consequently, the electric field is concentrated by the proximity of electric field lines 110, is non-uniform throughout the cell or embryo 120, and mainly affects the portion of the cell embryo 120 at the choke point. The positional dependency on the non-uniform electric field is susceptible to small deviations of the position of the cell or embryo 120 with respect to the first electroporation electrode 102 and the second electroporation electrode 104. This susceptibility can result in large changes to the position and efficiency of pore formation and makes reliable permeabilization difficult. Consequently, the membrane permeabilization is non-symmetrical and the reagent delivery is not as consistent as FIG. 1A or FIG. 1B.

Figure 3A:
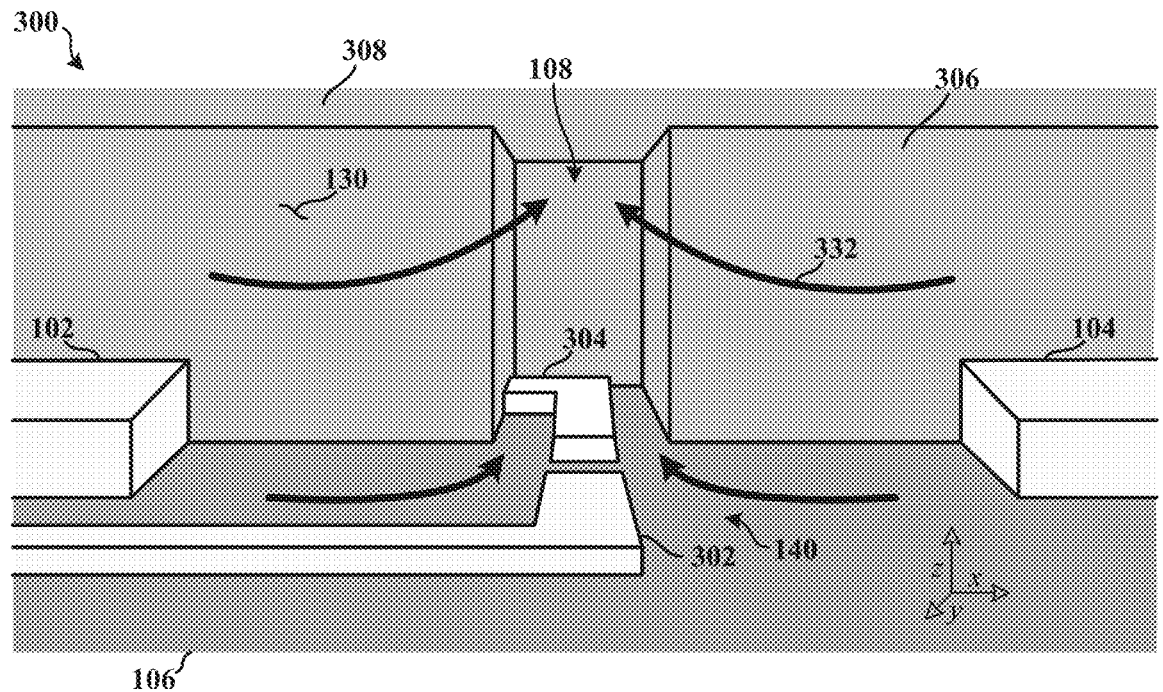
FIG. 3A illustrates an ISO view of exemplary microelectrode probe cell with microfluidic vents situated on a substrate between electroporation electrodes.

FIG. 3A illustrates an ISO view of an exemplary microelectrode probe cell 300 with microfluidic vents 108 situated on a substrate 106 between electroporation electrodes (e.g., the first electroporation electrode 102 and the second electroporation electrode 104). As depicted in FIG. 3A, a first electroporation electrode 102 and a second electroporation electrode 104 are situated on a substrate 106. In some examples, the substrate 106 has an electrically insulated surface that prevents the first electroporation electrode 102 from electrically shorting with the second electroporation electrode 104. In some examples, the substrate 106 lacks an electrically insulated surface.

The first electroporation electrode 102 and the second electroporation electrode 104 both have a surface that is substantially orthogonal to the electrically insulated surface (e.g., on the x-y plane) of the substrate 106. The second electroporation electrode 104 is separated a predetermined distance from the first electroporation electrode 102 at surfaces that are substantially orthogonal to the electrically insulated surface (e.g., on the x-y plane) of the substrate 106 so as to form a channel 140. In some examples, the predetermined distance between the first electroporation electrode 102 and the second electroporation electrode 104 is larger than the diameter of cell or embryo 120. In some examples, the predetermined distance between the first electroporation electrode 102 and the second electroporation electrode 104 is 50% to 200% of the diameter of the cell or embryo.

A fluidic vent 108 extends into a sidewall 306 that is situated on the surface (e.g., on the x-y plane) of the substrate 106. The sidewall 306 extends vertically in a direction (e.g., positive z-direction) orthogonal to the electrically insulated surface (e.g., on the x-y plane) of the substrate 106 and is a part of the microfluidic pipes. The vent 108 is smaller than the diameter of the cell or embryo 120 and is situated between the first electroporation electrode 102 and the second electroporation electrode 104. The vent 108 facilitates positioning of the cell or embryo 120 within the channel 140. In some examples, the substrate 106 includes one or more fluidic vents 108 situated within a second electrically insulated surface (e.g., on the x-y plane) of the substrate 106 between the one or both surfaces (e.g., the first surface and the second surface) of the first electroporation electrode 102 and the second electroporation electrode 104 that are substantially orthogonal to the electrically insulated surface (e.g., on the x-y plane) of the substrate 106. In such an instance, the second electrically insulated surface of the substrate is orthogonal to one or both surfaces (e.g., the first surface and the second surface) of the first electroporation electrode 102 and the second electroporation electrode 104 that are substantially orthogonal to the electrically insulated surface (e.g., on the x-y plane) of the substrate 106.

A second substrate 308 with a second electrically insulated surface is situated above the channel 140. As depicted in FIG. 3A, the second electrically insulated surface is substantially parallel to the first electrically insulated surface (e.g., x-y plane). The second substrate 308 is separated from the first electrically insulated surface a second predetermined distance, which facilitates to position the cell or embryo within the channel 140 between the first electroporation electrode 102 and the second electroporation electrode 104. In some examples, the second predetermined distance is 100% to 250% of the diameter of the cell or the embryo. In some examples, the second predetermined distance is 50% to 200%, 50% to less than 100%, or even 10% to 50% of the diameter of the cell or the embryo. In some examples, the substrate 106 is glass or silicon. In some instances, the glass is selected from the group consisting of Pyrex 7740, BK7 glass, Borofloat 33, Corning Eagle glass, D263, Gorilla glass, and soda-lime glass. In some examples, the second substrate 308 is fused silica quartz or single crystal quartz. In some examples, the second substrate 308 is silicon-on-insulator (SOI). In some instances, the silicon-on-insulator (SOI) is selected from the group consisting of silicon nitride on silicon and silicon-oxide on silicon. In some examples, the second substrate 308 is germanium or germanium-on-insulator. In some examples, the second substrate 308 is zinc oxide. In some examples, the second substrate 308 is a polymer. In some instances, the polymer is selected from the group consisting of Cast acrylic, ABS, nylon, polyethylene, cyclic olefin copolymer and polymer, acetal, polycarbonate, PETG, polyimide, FEP, PTFE, Polystyrene, polypropylene, silicone, PVC, polyurethane, PMMA, and PDMS. Epoxy resins can be UV curable such as SU-8, heat curable, or a dry film. In some examples, the second substrate 308 is polydimethylsiloxane. In some examples, the second substrate 308 is a low-temperature co-fired ceramic. In some examples, the second substrate 308 is a positive or negative photoresist. In some examples, sidewall 306 and second substrate 308 can both be the same material or different materials. They can both be made up of the materials used in the first electrically insulated layer (the base substrate with electrodes) or any of the polymers attached. The base layer, intermediary layer, and cover layer can all be the same material, each different, or any combination in between and still functionally act the same. The microfluidics used to position cells between the electrodes are made up of three layers. The base is the electrically insulated surface and can be any mix of silicon dioxide and other materials listed for substrate 106. The second intermediary layer makes up the side walls of the channel. The material can be the same as those used for substrate 106 or any of the polymers listed below. The final layer can also be made up of any material used for substrate 106 as well as any of the other polymers to house the electrode arrays.

A liquid medium 130 is situated within the channel 140 and is capable of supporting an electric field. As such, the liquid medium 130 does not electrically short the first electroporation electrode 102 to the second electroporation electrode 104. The liquid medium 130 can flow through the vent 108 (e.g., unobstructed) when a cell or embryo is not present. The liquid medium 130 can flow from the channel 140 into the vent 108 as branches of microfluidic flow 332, as depicted in FIG. 3A. The branches of microfluidic flow 332 of the liquid medium 130 are capable of transporting the cell or embryo 120 into the channel 140.

In addition to the first electroporation electrode 102 and the second electroporation electrode 104, the microelectrode probe can include a first sensing electrode 302 and a second sensing electrode 304. Both the first sensing electrode 302 and the second sensing electrode 304 are adjacent to the electrically insulated surface (e.g., on the x-y plane) of the substrate 106 and are situated adjacent to channel 140 or within the channel 140 to accommodate electrical contact between the first sensing electrode 302 and the second sensing electrode 304 and the cell or embryo 120. In some examples, cross sections of one or both of the first sensing electrode 302 and the second sensing electrode 304 are rectangular, triangular, trapezoidal, semi-circular, or semi-elliptical. In some examples, an edge length of one or both of the first sensing electrode 302 and the second sensing electrode 304 is less than an edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106. In some examples, an edge length of one or both of the first sensing electrode 302 and the second sensing electrode 304 ranges from 100 nm to 3.3 µm. In some examples, an edge length of one or both of the first sensing electrode 302 and the second sensing electrode 304 ranges from 100 nm to 40 µm. In some examples, the separation of the sensing electrodes ranges from 1% to 50% of the diameter of the embryo or cell.

In some examples, one or both of the first sensing electrode 302 and the second sensing electrode 304 include a hydrophilic surface coating. In some examples, the first sensing electrode 302 and the second sensing electrode is made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy (NiFe), graphene, indium tin oxide, tin, ruthenium, ruthenium oxide, rhodium, zirconium, TiNi, Al—Si—Cu, and cobalt. In some examples, one or both of the first sensing electrode 302 and the second sensing electrode 304 are made from a conductive alloy.

Signals provided to the first sensing electrode 302 and detected by the second sensing electrode 304 can indicate the status of the microelectrode probe and/or provide characteristics of the cell or embryo. For example, signals provided and/or sensed at the first sensing electrode 302 and the second sensing electrode 304 can be used to determine whether the cell is present in the channel 140. Likewise, the signals provided and/or sensed at the first sensing electrode 302 and the second sensing electrode 304 can determine the relative size of the cell or embryo 120. Signals can be placed across the first and second sensing electrodes and sensed at the first electrodes. Comparisons between what is observed and what was applied provide difference from which information can be extracted (i.e. attenuation of a signal, phase shift, frequency change). This may be performed at the main electroporating electrodes.

In some examples, the signals provided and sensed at the first sensing electrode 302 and/or the second sensing electrode 304 relate to the permeability of the cellular membrane. In some examples, the signals may be sensed at the electroporating electrodes. In some examples, the signals provided and/or sensed at the first sensing electrode 302 and the second sensing electrode 304 determine whether a liquid medium 130 is present. In some examples, the signals provided and/or sensed at the first sensing electrode 302 and the second sensing electrode 304 determine the concentration of reagents in the liquid medium 130. In some examples, the signals provided and/or sensed at the first sensing electrode 302 and the second sensing electrode 304 determine the ionic strength of the liquid medium 130. In some examples, the signals provided and/or sensed at the first sensing electrode 302 and the second sensing electrode 304 determine the cell stage (e.g., mitosis). In some examples, the signals provided and/or sensed at the first sensing electrode 302 and the second sensing electrode 304 determine the cell differentiation stage. In some examples, the signals provided and/or sensed at the first sensing electrode 302 and the second sensing electrode 304 are used to calculate the temperature of the liquid medium 130. In some examples, the signals provided and/or sensed at the first sensing electrode 302 and the second sensing electrode 304 calculate the fluidic flow 330. In some examples, the signals provided and/or sensed at the first sensing electrode 302 and the second sensing electrode 304 determine apoptosis. In some examples, the signals provided and/or sensed at the first sensing electrode 302 and the second sensing electrode 304 determine necrosis. In some examples, the signals provided and/or sensed at the first sensing electrode 302 and the second sensing electrode 304 are used to calculate a volume change in a cell or embryo 120. In some examples, the signals provided and/or sensed at the first sensing electrode 302 and the second sensing electrode 304 are used to calculate the growth rate of a cell or embryo 120. In some examples, the signals provided and/or sensed at the first sensing electrode 302 and the second sensing electrode 304 are used to calculate the ion-activity with the liquid medium 130.

It should be appreciated that a configuration of which sensing electrode provides a signal and which detects the signal can be reversed. For example, instead of signals being provided to the first sensing electrode 302 and detected by the second sensing electrode 304, the signals can be provide to the second sensing electrode 304 and detected by the first sensing electrode 302.

As depicted in FIG. 3A, the first sensing electrode 302 and the second sensing electrode 304 are provided adjacent to the electrically insulated surface (e.g., on the x-y plane) of the substrate 106. The first sensing electrode 302 and the second sensing electrode 304 are situated adjacent to channel 140 or within the channel 140 and situated so as to accommodate electrical contact between the first sensing electrode 302, the second sensing electrode 304, and the cell or embryo 120.

Figure 3B:
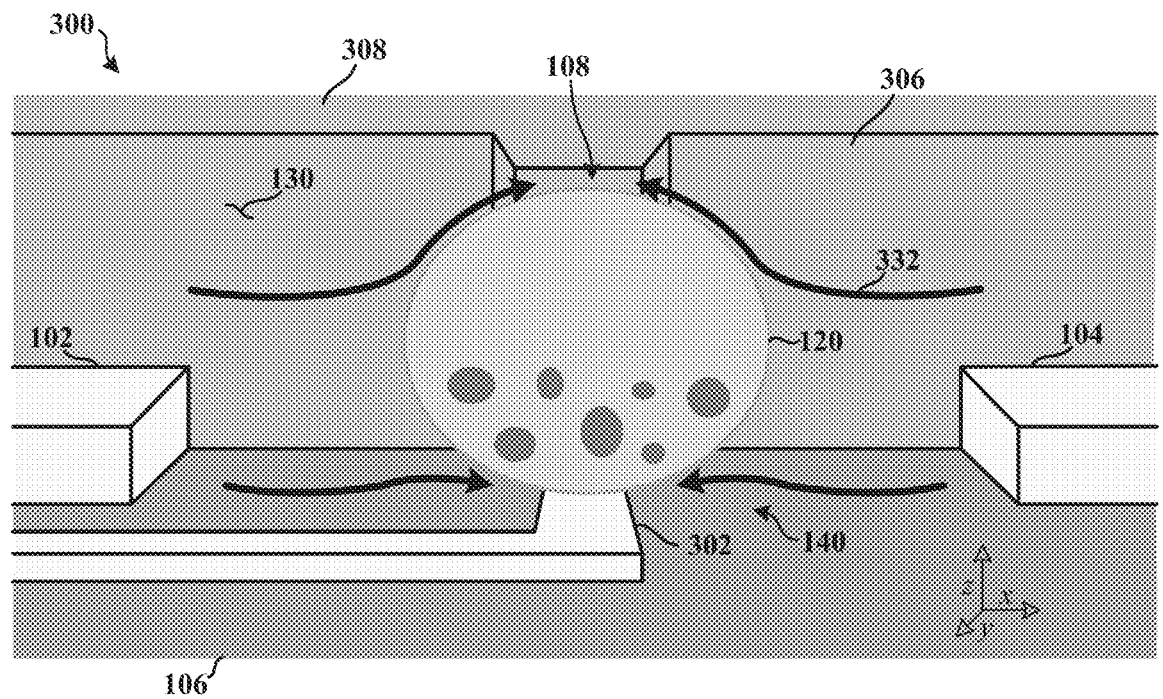
FIG. 3B illustrates an ISO view of an exemplary microelectrode probe with a cell or embryo drawn to the microfluidic vents situated on a substrate between electroporation electrodes.

FIG. 3B illustrates an ISO view of an exemplary microelectrode cell 300 with a cell or embryo 120 drawn to the microfluidic vents 108 and situated on a substrate between electroporation electrodes (e.g., the first electroporation electrode 102 and the second electroporation electrode 104). In this instance, the branches of microfluidic flow 332 draw the cell or embryo 120 to the vent 108. Although not depicted, in some examples, a portion of the sidewall 306 at the vent 108 is angled. The angled surface at the vents 108 causes the cell or embryo 120 to be positioned proximate the substrate 106 so as to contact the sensing electrodes (e.g., first sensing electrode 302 and second sensing electrode 304). In some examples, the entire the sidewall 306 is angled (e.g., non-orthogonal to the insulated surface (e.g., on the x-y plane) of the substrate 106).

A second substrate 308 with a second electrically insulated surface is situated above the channel 140. As depicted in FIG. 3B, the second electrically insulated surface is substantially parallel to the first electrically insulated surface (e.g., x-y plane). The second substrate 308 is separated from the first electrically insulated surface a second predetermined distance, which facilitates to position the cell or embryo within the channel 140 between the first electroporation electrode 102 and the second electroporation electrode 104. In some examples, the second predetermined distance may be 100% to 250% of the diameter of the cell or the embryo. In some examples, the second predetermined distance may be 50% to 200%, 50% to less than 100%, or even 10% to 50% of the diameter of the cell or the embryo. A liquid medium 130 is situated within the channel 140 between the substrate 106 and the second substrate 308. The liquid medium 130 is capable of supporting an electric field and does not electrically short the first electroporation electrode 102 to the second electroporation electrode 104.

The presence of the cell or embryo 120 obstructs the branches of microfluidic flow 332 in the channel 140 through the vent 108. In some examples, the branches of microfluidic flow 332 are reduced but continue to flow despite the presences of the cell or embryo 120, as depicted in FIG. 3B. In some instances, the cell or embryo 120 completely covers the vent 108 and the branches of microfluidic flow 332 are blocked.

In some examples, the vent 108 has an opening that is larger in a region over the sensing electrodes (e.g., first sensing electrode 302 and second sensing electrode 304) than in a region distal from the sensing electrodes (e.g., first sensing electrode 302 and second sensing electrode 304). In some instances, this larger opening to the vent 108 facilitates positioning the cell or embryo 120 proximate the substrate 106 so as to contact the sensing electrodes (e.g., first sensing electrode 302 and second sensing electrode 304). In some examples, the vent 108 has an opening that is smaller in a region over the sensing electrodes (e.g., first sensing electrode 302 and second sensing electrode 304) than in a region distal from the sensing electrodes (e.g., first sensing electrode 302 and second sensing electrode 304). In some instances, this smaller opening to the vent 108 facilitates positioning the cell or embryo 120 proximate to the substrate 106 so as to contact the sensing electrodes (e.g., first sensing electrode 302 and second sensing electrode 304). In some examples, the liquid medium 130 that flows through the vents 108 positions the cell or embryo within the channel 140 between the first electroporation electrode 102 and the second electroporation electrode 104 and onto the first sensing electrode 302 and second sensing electrode 304.

In some examples, the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 0.02% to 75.0% of the diameter of the cell or embryo. In some examples, the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 1 μm to 1 mm. In some examples, the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 5 μm to 100 μm. In some examples, an edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 0.02% to 100.0% of the diameter of the cell or embryo 120.

The microelectrode configuration for single cell electroporation is partly defined by the electrode height, electrode width, and electrode separation, which are each dependent on the diameter of the cell being electroporated. To target only a sub-portion of the cell the height range for microelectrode utilization is between 0.002% and 100% of the cell's diameter.

Electrode width is variable to the effectiveness of the microfluidic or isolation network utilizing the microelectrode configuration. Integrated into a system with high isolation accuracy the range for Electrode Widths would be between 10% and 200% of the cell's diameter. Anything less than the diameter of the cell is to further confine the surface area of the cell being porated in addition to the height limitations. With a low isolation accuracy, a wider set of electrodes could be used with a range between 200% and 1000% of the cell's diameter.

Electrode separation changes the surface area of the cell in direct and intimate contact with the electrodes. A high degree of contact would be useful when attempting to maximize pore formation and membrane destabilization for greater reagent uptake however also would result in higher cell death. This range is 10% to 50% of the cell's diameter. A more intermediate range allows the cells to come in contact with one electrode or the other but not both at the same time given the curvature of the cell membrane. This range is between 50% and 200% of the cell's diameter. A high viability but low effective range for the electrode separation is between 200% and 1000% of the cell's diameter which is useful when attempting to work with sensitive cells such as those out of cryo preservation or requiring less direct electroporation.

Table 3 below lists the parameters based on cell type and cell class, where the EP electrode height is 0.02% to 100% of the cell diameter, the EP electrode separation is 50% to 200% of the cell diameter, and the EP electrode width is 10% to 200% of the cell diameter. The parameters mentioned above for the size ranges of the microelectrodes are all cell diameter dependent and can apply to alternate developed or engineered lines and those not directly mentioned in the chart. Any rotation of the electrodes effectively resulting in partial electroporation constitutes as partial membrane electroporation as described herein. Each of the three dimensions can be changed independent to the other electrodes and so long as each dimension falls within an acceptable range, any combination of the electrode dimensions constitute a microelectrode.

the cell or embryo 120. In some examples, the predetermined distance ranges from 1× the diameter of the cell to 1.25× the diameter of the cell or embryo 120. For example, in some configurations, the microelectrode cell 300 is for electroporation of mammalian embryos and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 100 nm to 120 µm. In such configuration, the predetermined distance ranges from 80 µm to 200 µm.

In some configurations, the microelectrode cell 300 is for electroporation of insect embryo cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 0.18 mm to

TABLE 3

| Cell Type | | Diameter Range (Lower Bound-Upper Bound) | Electrode Height (.02%-100% Cell Diameter) | Electrode Separation: High Cell Surface Area Contact with Electrodes (10%-50% cell diameter) | Electrode Separation: Low Cell Surface Area Contact with Electrodes (50%-200% cell diameter) |
|---|---|---|---|---|---|
| Embryos | Mammalian | 60 µm-160 µm | 100 nm-160 µm | 6 µm-30 µm | 30 µm-320 µm |
| | Insect | 0.18 mm-16.5 mm | 100 nm-16.5 mm | 18 µm-90 µm | 0.09 m-33 mm |
| | Amphibian | 1 mm-2 mm | 100 nm-2 mm | 100 µm-500 µm | 0.5 mm-4 mm |
| | Fish | .7 mm-9 mm | 100 nm-9 mm | 70 µm-450 µm | 0.45 mm-18 mm |
| Plants/Fungi | Plant Protoplasts | 10 µm-40 µm | 100 nm-40 µm | 1 µm-5 µm | 5 µm-80 µm |
| | Pollen | 6 µm-120 µm | 100 nm-120 µm | .6 µm-3 µm | 3 µm-240 µm |
| | Fungi Protoplast | 2 µm-5 µm | 100 nm-5 µm | .2 µm-1 µm | 1 µm-10 µm |
| | Yeast | 3 µm-4 µm | 100 nm-4 µm | .3 µm-1.5 µm | 1.5 µm-8 µm |
| Mammalian Cell Lines | Immune | 5 µm-80 µm | 100 nm-80 µm | .5 µm-2.5 µm | 2.5 µm-160 µm |
| | Connective Tissue | 2 µm-20 µm | 100 nm-20 µm | .2 µm-1 µm | 1 µm-40 µm |
| | Endothelial | 10 µm-20 µm | 100 nm-20 µm | 1 µm-5 µm | 5 µm-40 µm |
| | Epithelial | 10 µm-120 µm | 100 nm-120 µm | 1 µm-5 µm | 5 µm-240 µm |
| | Muscle | 10 µm-40 mm | 200 nm-40 mm | 1 µm-5 µm | 5 µm-80 mm |
| | Mesenchymal Stem | 20 µm-30 µm | 100 nm-30 µm | 2 µm-10 µm | 10 µm-60 µm |
| | Embryonic Stem | 10 µm-15 µm | 100 nm-15 µm | 1 µm-5 µm | 5 µm-30 µm |
| | IPSC | 10 µm-30 µm | 100 nm-30 µm | 1 µm-5 µm | 5 µm-60 µm |
| | CHO | 10 µm-15 µm | 100 nm-15 µm | 1 µm-5 µm | 5 µm-30 µm |
| | HeLA | 10 µm-20 µm | 100 nm-20 µm | 1 µm-5 µm | 5 µm-40 µm |
| | HEK293 | 10 µm-15 µm | 100 nm-15 µm | 1 µm-5 µm | 5 µm-30 µm |

| | Cell Type | | Electrode Separation: No Cell Surface Area Contact with Electrodes (200%-1000% cell diameter) | Electrode Width: Precise Single Cell Isolation (10%-200%) | Electrode Width: Poor Single Cell Isolation (10%-1000%) |
|---|---|---|---|---|---|
| Embryos | Mammalian | | 320 µm-160 mm | 6 µm-320 µm | 6 µm-160 mm |
| | Insect | | 33 mm-1 m | 18 µm-33 mm | 18 µm-1 m |
| | Amphibian | | 500 µm-1 m | 100 µm-4 mm | 100 µm-1 m |
| | Fish | | 18 mm-1 m | 70 µm-18 mm | 70 µm-1 m |
| Plants/Fungi | Plant Protoplasts | | 80 µm-40 mm | 1 µm-80 µm | 1 µm-40 mm |
| | Pollen | | 240 µm-120 mm | 0.6 µm-240 µm | 0.6 µm-120 mm |
| | Fungi Protoplast | | 10 µm-5 mm | 0.2 µm-10 µm | 0.2 µm-5 mm |
| | Yeast | | 8 µm-4 mm | 0.3 µm-8 µm | 0.3 µm-4 mm |
| Mammalian Cell Lines | Immune | | 160 µm-80 mm | 0.5 µm-160 µm | 0.5 µm-80 mm |
| | Connective Tissue | | 40 µm-20 mm | 0.2 µm-40 µm | 0.2 µm-20 mm |
| | Endothelial | | 40 µm-20 mm | 1 µm-40 µm | 1 µm-20 mm |
| | Epithelial | | 240 µm-120 mm | 1 µm-240 µm | 1 µm-120 mm |
| | Muscle | | 80 mm-40 mm | 1 µm-80 µm | 1 µm-40 mm |
| | Mesenchymal Stem | | 60 µm-30 mm | 2 µm-60 µm | 2 µm-30 mm |
| | Embryonic Stem | | 30 µm-15 mm | 1 µm-30 µm | 1 µm-15 mm |
| | IPSC | | 60 µm-30 mm | 1 µm-60 µm | 1 µm-30 mm |
| | CHO | | 30 µm-15 mm | 1 µm-30 µm | 1 µm-15 mm |
| | HeLA | | 40 µm-20 mm | 1 µm-40 µm | 1 µm-20 mm |
| | HEK293 | | 30 µm-15 mm | 1 µm-30 µm | 1 µm-15 mm |

In some examples, the predetermined distance ranges from 0.75× the diameter of the cell to 1.5× the diameter of 3 mm. In such configuration, the predetermined distance ranges from 0.18 mm to 3.75 mm. It should be appreciated that insect embryo cells are oblong and vary in size. Ranges for shorter lengths of insect embryo cells range from 0.18 mm to 3.75 mm, whereas ranges for longer lengths of the same insect embryo cells range from 0.5 mm to 20.63 mm.

In some configurations, the microelectrode cell 300 is for electroporation of insect embryo cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 0.5 mm to 16.5 mm. In such configuration, the predetermined distance ranges from 0.5 mm to 20.63 mm.

In some configurations, the microelectrode cell 300 is for electroporation of amphibian embryo cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 1 mm to 2 mm. In such configuration, the predetermined distance ranges from 1 mm to 2.5 mm.

In some configurations, the microelectrode cell 300 is for electroporation of fish embryo cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 0.7 mm to 9 mm. In such configuration, the predetermined distance ranges from 0.7 mm to 11.25 mm.

In some configurations, the microelectrode cell 300 is for electroporation of plant protoplasts and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 μm to 40 μm. In such configuration, the predetermined distance ranges from 10 μm to 50 μm.

In some configurations, the microelectrode cell 300 is for electroporation of pollen and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 6 μm to 120 μm. In such configuration, the predetermined distance ranges from 6 μm to 150 μm.

In some configurations, the microelectrode cell 300 is for electroporation of fungi protoplasts and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 2 μm to 5 μm. In such configuration, the predetermined distance ranges from 2 μm to 6.5 μm.

In some configurations, the microelectrode cell 300 is for electroporation of yeast and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 3 μm to 4 μm. In such configuration, the predetermined distance ranges from 3 μm to 5 μm.

In some configurations, the microelectrode cell 300 is for electroporation of mammalian immune cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 5 μm to 80 μm. In such configuration, the predetermined distance ranges from 5 μm to 100 μm.

In some configurations, the microelectrode cell 300 is for electroporation of mammalian connective tissue cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 2 μm to 20 μm. In such configuration, the predetermined distance ranges from 2 μm to 25 μm.

In some configurations, the microelectrode cell 300 is for electroporation of mammalian endothelial cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 μm to 20 μm. In such configuration, the predetermined distance ranges from 10 μm to 25 μm.

In some configurations, the microelectrode cell 300 is for electroporation of mammalian epithelial cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 μm to 120 μm. In such configuration, the predetermined distance ranges from 10 μm to 150 μm.

In some configurations, the microelectrode cell 300 is for electroporation of mammalian muscle cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 μm to 100 μm. In such configuration, the predetermined distance ranges from 10 μm to 125 μm. It should be appreciated that mammalian muscle cells are oblong and vary in size. Ranges for shorter lengths of mammalian muscle cells range from 10 μm to 125 μm, whereas ranges for longer lengths of the same mammalian muscle cells range from 1 mm to 125 mm.

In some configurations, the microelectrode cell 300 is for electroporation of mammalian muscle cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 1 mm to 40 mm. In such configuration, the predetermined distance ranges from 1 mm to 50 mm.

In some configurations, the microelectrode cell 300 is for electroporation of mammalian mesenchymal stem cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 20 µm to 30 µm. In such configuration, the predetermined distance ranges from 20 µm to 37.5 µm.

In some configurations, the microelectrode cell 300 is for electroporation of mammalian embryonic stem cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 µm to 15 µm. In such configuration, the predetermined distance ranges from 10 µm to 18.75 µm.

In some configurations, the microelectrode cell 300 is for electroporation of mammalian IPSC cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 µm to 30 µm. In such configuration, the predetermined distance ranges from 20 µm to 37.5 µm.

In some configurations, the microelectrode cell 300 is for electroporation of mammalian CHO cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 µm to 15 µm. In such configuration, the predetermined distance ranges from 10 µm to 18.75 µm.

In some configurations, the microelectrode cell 300 is for electroporation of mammalian HeLA cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 µm to 20 µm. In such configuration, the predetermined distance ranges from 10 µm to 25 µm.

In some configurations, the microelectrode cell 300 is for electroporation of mammalian HEK293 cells and the edge length of one or both of the substantially orthogonal surfaces (e.g., first surface and the second surface) of the first electroporation electrode 102 and the second electroporation electrode 104 that extends in a direction (e.g., positive z-direction) orthogonal to the electrically insulated surface (e.g., on the x-y plane) of the substrate 106 ranges from 10 µm to 15 µm. In such configuration, the predetermined distance ranges from 10 µm to 18.75 µm.

Figures 4A, 4B:
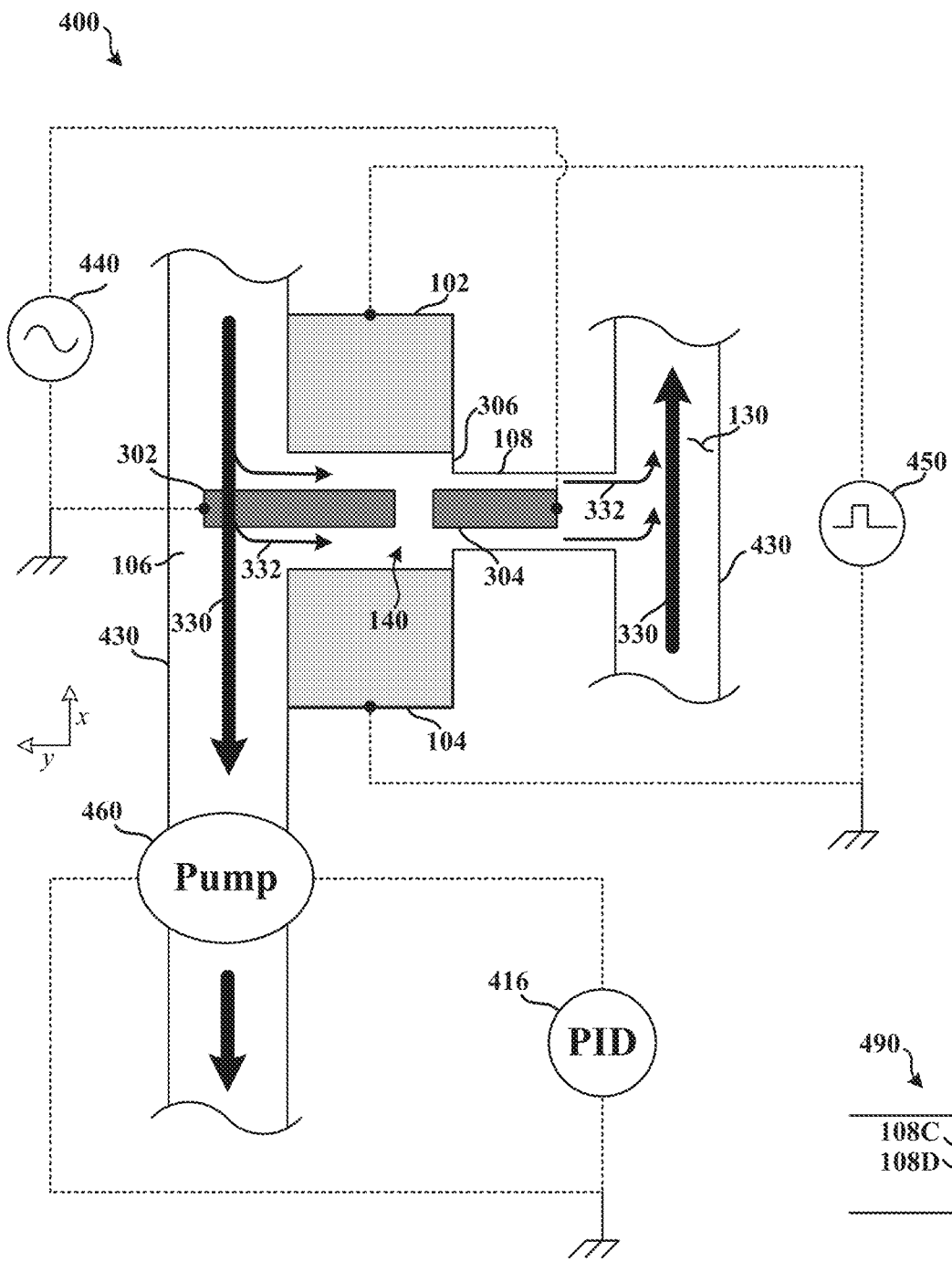
FIG. 4A illustrates a cross-sectional view of a microelectrode probe cell.
FIG. 4B illustrates a fluidic vent comprising a plurality of identical smaller vents in parallel.

FIG. 4A illustrates a cross-sectional view of a microelectrode probe cell 400. As depicted in FIG. 4A, a first electroporation electrode 102 and a second electroporation electrode 104 are situated on a substrate 106. The first electroporation electrode 102 and a second electroporation electrode 104 are electrically separated by the substrate 106 and the liquid medium 130. The substrate 106 has an electrically insulated surface that prevents the first electroporation electrode 102 from electrically shorting with the second electroporation electrode 104. The liquid medium 130 is situated within the channel 140 and within the microfluidic pipes 430. The liquid medium 130 is capable of supporting an electric field and does not electrically short the first electroporation electrode 102 to the second electroporation electrode 104.

The first electroporation electrode 102 and the second electroporation electrode 104 both have a surface (e.g., on the y-z plane) that is substantially orthogonal to the electrically insulated surface (e.g., on the x-y plane) of the substrate 106. The second electroporation electrode 104 is separated a predetermined distance from the first electroporation electrode 102 at surfaces (e.g., on the x-z plane) that are substantially orthogonal to the electrically insulated surface (e.g., on the x-y plane) of the substrate 106, which forms channel 140. The predetermined distance between the first electroporation electrode 102 and the second electroporation electrode 104 is larger than the diameter of cell or embryo 120.

A pulse generator 450 is electrically coupled to the first electroporation electrode 102 and the second electroporation electrode 104, as depicted in FIG. 4A. The pulse generator 450 is configured to generate a signal (e.g., inject a signal) so that the first electrode and/or the second electrode induces a uniform electric field with substantially parallel electric field lines between the surfaces (e.g., the first surface and the second surface) of the first electroporation electrode 102 and the second electroporation electrode 104 that are substantially orthogonal to the electrically insulated surface (e.g., on the x-y plane) of the substrate 106. In some examples, the generated pulse is a sinusoid waveform or a non-sinusoidal waveform. In some instances, the non-sinusoidal waveform is a square waveform, a triangular waveform, or a saw-tooth waveform. In some examples, the generated pulse has a frequency between 1 Hz to 1 kHz. In some examples, the generated pulse has a frequency between 1 Hz to 5 kHz. In some examples, the generated pulse has a duty cycle of 50%. In some examples, the generated pulse induces an electric field that ranges between 100 V/cm to 4 kV/cm. In some examples, the generated pulse induces an electric field that ranges between 10 V/cm to 5 kV/cm, accommodating extremely safe delivery. In some examples, the sensing setup is also connected in parallel to the pulse generator to the electroporating electrodes through a multiplexing circuit which allows for controlled selection of what is immediately affecting the electrodes via a computer or controller.

In some examples, the pulse generator 450 is a standalone pulse generator electrically coupled to the microcontroller/computer. In some instances, the standalone pulse generator 450 uses a serial connector (e.g., universal serial bus (USB), serial port (RS-232 standard), Ethernet, FireWire, SPI, I2C, etc.) or a parallel connector (e.g., parallel port, enhanced parallel port (EPP), and extended capability port (ECP), etc.) to electrically couple to the microcontroller/computer. In some instances, the standalone pulse generator 450 uses a general purpose interface bus (GPIB) to electrically couple to the microcontroller/computer. In some examples, the pulse generator 450 includes a bi-directional multiplexer electrically coupled to the first electroporation electrode 102 and the second electroporation electrode 104 that is configured to fire a pulse to the first electroporation electrode 102 and/or the second electroporation electrode 104. In some instances, a monostable multivibrator may be used as the module to create a square pulse.

A first sensing electrode 302 and a second sensing electrode 304 are electrically separated by the substrate 106 and the liquid medium 130. Signals provided (e.g., injected) to the first sensing electrode 302 and detected by the second sensing electrode 304 can indicate the status of the microelectrode probe and/or provide characteristics of the cell or embryo. A signal generator 440 is configured to provide such signals. In some examples, the generated signal is a sinusoid waveform or a non-sinusoidal waveform. In some instances, the non-sinusoidal waveform is an exponential waveform, a square waveform, a triangular waveform, or a saw-tooth waveform. In some examples, the generated signal has a frequency between 1 Hz to 1 kHz. In some examples, the generated signal has a duty cycle of 50%. The above may be applied to the electroporating electrodes and the signal may be extracted from either sensing electrode. The frequency range may be extended significantly to a range of 1 Hz to 100 GHz; embryo sensing will be in the kHz to MHz range, so that detailed-feature extraction will require large frequencies. In some examples, chip sensors may aid in the identification of whether an electrode is surrounded by air, liquid, or the residue of liquid after it has left the chip. A 60 Hz sinusoidal signal (or other waveforms such as triangular, exponential, and square) is applied to an electrode and its attenuation is measured at the same electrode. When a signal amplitude experiences an abrupt increase or decrease, the type of surrounding on-chip may be ascertained: For example, a drop of signal of 37.5% within 4 ms indicates an air-to-liquid transition. For example, a rise of signal of 30% within 4 ms indicates an liquid-to-residue transition. Attenuation measurement via this method is used to ensure electrical pulses are accurately delivered to the first and second electroporating electrodes. A pulse is first delivered to the electrodes, the voltage is then measured, and stored. This stored value is compared to a calculated one which corresponds to a perfect pulse. If there is a difference the pulsing module is adjusted towards the calculated value and the entire process loops until the two are identical.

As depicted in FIG. 4A, the signal generator 440 is electrically coupled to the first sensing electrode 302 and the second sensing electrode 304. In some examples, the signal generator 440 is a standalone signal generator electrically coupled to the microcontroller/computer. In some instances, the standalone signal generator 440 uses a serial connector (e.g., universal serial bus (USB), serial port (RS-232 standard), Ethernet, FireWire, I2C, SPI) or a parallel connector (e.g., parallel port, enhanced parallel port (EPP), and extended capability port (ECP)) to electrically couple to the microcontroller/computer. In some instances, the standalone signal generator 440 uses a general purpose interface bus (GPIB) to electrically couple to the microcontroller/computer. In some examples, the signal generator 440 includes a bi-directional multiplexer electrically coupled to the first sensing electrode 302 and the second sensing electrode 304 that is configured to provide a signal to the first sensing electrode 302 and/or the second sensing electrode 304. In some examples, the signal generator 440 and the signal extractor may be two parallel circuits. In some examples, the signal extractor may be connected to any of the four electrodes regardless of the signal generator or pulse generator setup.

A fluidic vent 108 extends into a sidewall 306 that is situated on the surface (e.g., on the x-y plane) of the substrate 106. The sidewall 306 extends vertically in a direction (e.g., positive z-direction) orthogonal to the insulated surface (e.g., on the x-y plane) of the substrate 106 and is a part of the microfluidic pipes 430. The vent 108 is smaller than the diameter of the cell or embryo 120 and is situated between the first electroporation electrode 102 and the second electroporation electrode 104. The vent 108 is configured to position the cell or embryo 120 within the channel 140. In some examples, the vents 108 are straight and orthogonal to the substrate 106 (vent 108 of FIG. 4A). In some instances, the vents 108 are rounded.

As shown in FIG. 4B, in some examples, the vent 108 may comprise a plurality of identical smaller vents 108C and 108D arranged in parallel or in any angled configuration.

Pressure differentials within the microfluidic pipes 430 cause fluidic flow 330 of the liquid medium 130 and transport of the cell or embryo 120. The pressure differences may be created with a pump (e.g. a syringe pump). The (liquid) current of the fluidic flow 330 can be greater than the (liquid) current of the branches of microfluidic flow 332 through the channel 140A of cell A and vents 108. As depicted in FIG. 4A, branches of the microfluidic flow 332 are directed into the channel 140 and through the vent 108 and out of the channel 140. A pump 460 is hermetically coupled to the microfluidic pipes 430. In some examples, the pump 460 is configured to adjust fluidic flow 330 in response to a proportional, integral, derivative (PID) 416 algorithm controller that is electrically coupled to the pump 460. The PID controller continuously calculates an error value as the difference between a desired setpoint and a measured process variable and applies a correction based on proportional, integral, and derivative terms. In some examples, the PID is integrated into a microcontroller/computer (e.g., pump controller 616 FIG. 6). In some examples, a PID controller is not used, and instead, liquid air residue (LAR) and embryo sensing across the chip enable an algorithm to control fluid movement, embryo trapping, and embryo recovery. This algorithm, in addition to the monitoring of these states, takes advantage of known features in the chip's design.

Figure 5:
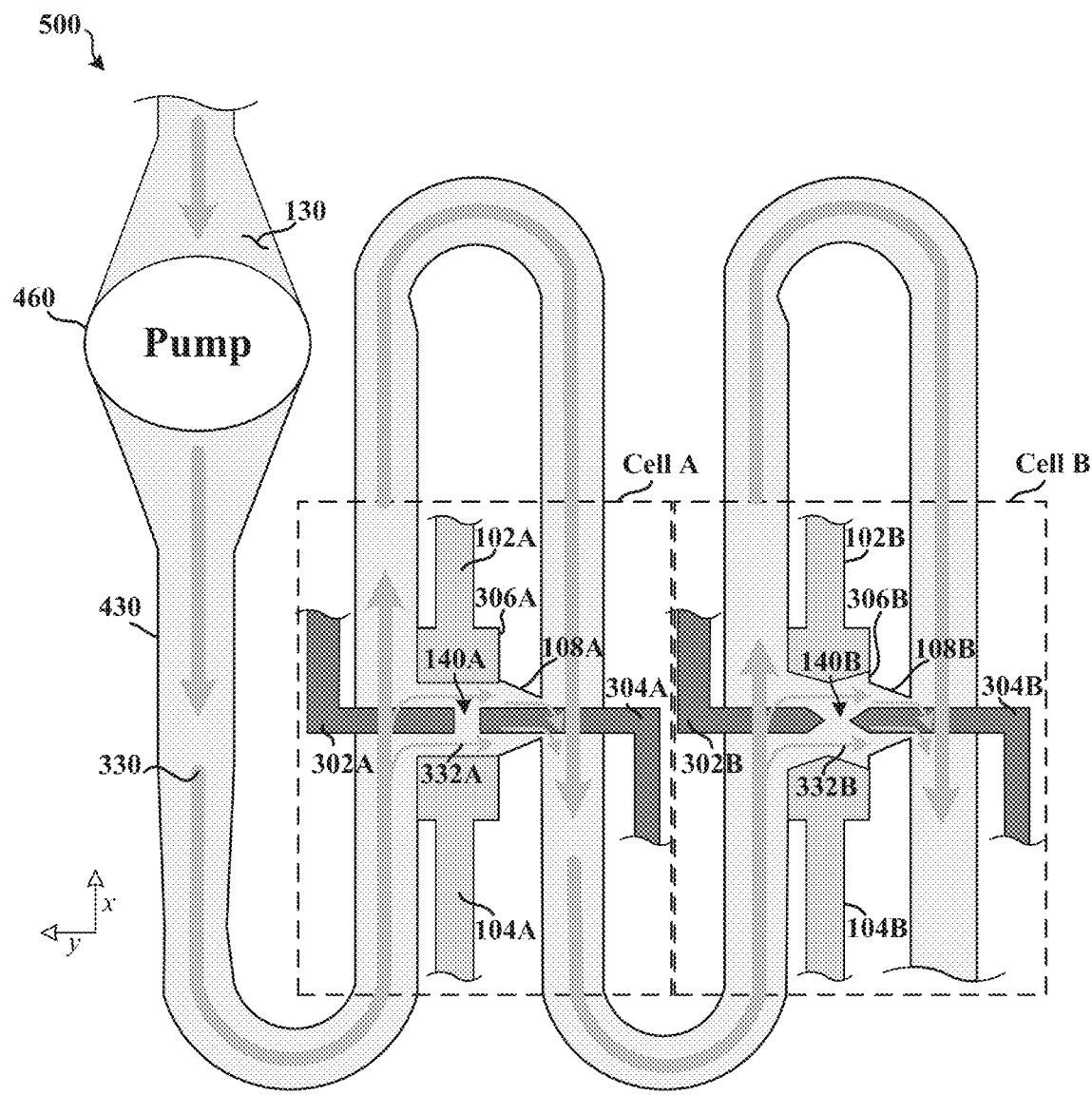
FIG. 5 illustrates a cross-sectional view of a microelectrode probe array.

FIG. 5 illustrates a cross-sectional view of a microelectrode probe array 500. The microelectrode probe cell 400 of FIG. 4A can be reproduced in cell A, cell B, etc. For example, a first electroporation electrode 102A of cell A and a second electroporation electrode 104A of cell A are electrically separated by the substrate 106 and the liquid medium 130. In some examples, the substrate 106 has an electrically insulated surface. The first electroporation electrode 102A of cell A and the second electroporation electrode 104A of cell A form polyhedral surfaces that are substantially orthogonal to the electrically insulated surface (e.g., on the x-y plane) of the substrate 106 and parallel to each other.

The first electroporation electrode 102A of cell A and the second electroporation electrode 104A of cell A both have a surface that is substantially orthogonal to the electrically insulated surface (e.g., on the x-y plane) of the substrate 106. The second electroporation electrode 104A of cell A is separated a predetermined distance from the first electroporation electrode 102A of cell A at surfaces that are substantially orthogonal to the electrically insulated surface (e.g., on the x-y plane) of the substrate 106, which forms channel 140A of cell A. In some examples, the predetermined distance between the first electroporation electrode 102A of cell A and the second electroporation electrode 104A of cell A is larger than the diameter of cell or embryo 120. In some examples, the predetermined distance between the first electroporation electrode 102A of cell A and the second electroporation electrode 104A of cell A is 50% to 200%, 50% to less than 100%, or even 10% to 50% of the diameter of cell or embryo 120.

The liquid medium 130 is situated within the channel 140A of cell A and within the microfluidic pipes 430. The liquid medium 130 is capable of supporting an electric field and therefore does not electrically short the first electroporation electrode 102A of cell A to the second electroporation electrode 104A of cell A.

Although not depicted in FIG. 5, a pulse generator 450 is electrically coupled to the first electroporation electrode 102A of cell A and the second electroporation electrode 104A of cell A, as depicted in FIG. 4A. The pulse generator 450 can be a standalone pulse generator electrically coupled to a microcontroller/computer. The electrical coupling between the standalone pulse generator 450 and the microcontroller/computer can be a serial connector (e.g., universal serial bus (USB), serial port (RS-232 standard), Ethernet, FireWire, I2C, SPI, etc.) or a parallel connector (e.g., parallel port, enhanced parallel port (EPP), and extended capability port (ECP), etc.) or a general purpose interface bus (GPIB). In some examples, the pulse generator 450 includes a bi-directional multiplexer electrically coupled to the first electroporation electrode 102A of cell A and the second electroporation electrode 104A of cell A that is configured to fire a pulse to the first electroporation electrode 102A of cell A and/or the second electroporation electrode 104A of cell A.

A first sensing electrode 302A of cell A and a second sensing electrode 304A of cell A are also electrically separated by the substrate 106 and the liquid medium 130. The first sensing electrode 302B of cell B and the second sensing electrode 304B of cell B form polyhedral surfaces that are substantially orthogonal to the electrically insulated surface (e.g., on the x-y plane) of the substrate 106 and are parallel to each other. Although not depicted in FIG. 5, a signal generator 440 is electrically coupled to the first sensing electrode 302A of cell A and the second sensing electrode 304A of cell A, as depicted in FIG. 4A. The signal generator 440 can be a standalone signal generator electrically coupled to a microcontroller/computer. The electrical coupling between the standalone signal generator 440 and the microcontroller/computer can be a serial connector (e.g., universal serial bus (USB), serial port (RS-232 standard), Ethernet, FireWire, etc.) or a parallel connector (e.g., parallel port, enhanced parallel port (EPP), and extended capability port (ECP), I2C, SPI) or a general purpose interface bus (GPIB). In some examples, the signal generator 440 includes a bi-directional multiplexer electrically coupled to the first sensing electrode 302A of cell A and the second sensing electrode 304A of cell A that is configured to provide a signal to the first sensing electrode 302A of cell A and/or the second sensing electrode 304A of cell A.

Cell B is similar to and electrically isolated from cell A. Cell B includes a first electroporation electrode 102B of cell B and a second electroporation electrode 104B of cell B which are electrically separated by the substrate 106 and the liquid medium 130. The first electroporation electrode 102B of cell B and the second electroporation electrode 104B of cell B form polyhedral surfaces that are substantially orthogonal to the electrically insulated surface (e.g., on the x-y plane) of the substrate 106 and are not parallel to each other.

In some examples, the polyhedral surfaces are applicable to electrode adjacent faces, namely the faces on the side facing the other electrode, namely are parallel to the cross-sectional area in the y-z plane in FIG. 5. In some examples, one or both of the polyhedral surfaces are curved. In some examples, one or both of the polyhedral surfaces are semi-circular or semi-elliptical. In some examples, one or both of the polyhedral surfaces are rectangular, triangular, or trapezoidal. In some examples, one or both of the polyhedral surfaces form a polyhedron situated on a cross-sectional end of the first electroporation electrode 102B of cell B and/or the second electroporation electrode 104B of cell B. In some instances, the polyhedron situated on a cross-sectional end of the first electroporation electrode 102B of cell B and/or the second electroporation electrode 104B of cell B forms a triangular prism, a quadrahedron, a pentahedron, a hexahedron, a septaheron, or an octahedron. In some instances, the polyhedron situated on a cross-sectional end of the first electroporation electrode 102B of cell B and/or the second electroporation electrode 104B of cell B forms a triangular prism, a quadrahedron, a pentahedron, a hexahedron, a septaheron, or an octahedron The substrate 106 has an electrically insulated surface that prevents the first electroporation electrode 102B of cell B from electrically shorting with the second electroporation electrode 104B of cell B. The liquid medium 130 is situated within the channel 140B of cell B and within the microfluidic pipes 430. The liquid medium 130 is capable of supporting an electric field and therefore does not electrically short the first electroporation electrode 102B of cell B to the second electroporation electrode 104B of cell B.

The first electroporation electrode 102B of cell B and the second electroporation electrode 104B of cell B both have a surface that is substantially orthogonal to the electrically insulated surface (e.g., on the x-y plane) of the substrate 106. The second electroporation electrode 104B of cell B is separated a predetermined distance from the first electroporation electrode 102B of cell B at surfaces that are substantially orthogonal to the electrically insulated surface (e.g., on the x-y plane) of the substrate 106, which forms channel 140B of cell B. In some examples, the predetermined distance between the first electroporation electrode 102B of cell B and the second electroporation electrode 104B of cell B is larger than the diameter of cell or embryo 120. In some examples, the predetermined distance between the first electroporation electrode 104B of cell B and the second electroporation electrode 104B of cell B is 50% to 200% of the diameter of cell or embryo 120.

Although not depicted in FIG. 5, a pulse generator 450 is electrically coupled to the first electroporation electrode 102B of cell B and the second electroporation electrode 104B of cell B, as depicted in FIG. 4A. The pulse generator 450 can be a standalone pulse generator electrically coupled to a microcontroller/computer. The electrical coupling between the standalone pulse generator 450 and the microcontroller/computer can be a serial connector (e.g., universal serial bus (USB), serial port (RS-232 standard), Ethernet, FireWire, I2C, SPI) or a parallel connector (e.g., parallel port, enhanced parallel port (EPP), and extended capability port (ECP), etc.) or a general purpose interface bus (GPIB). In some examples, the pulse generator 450 includes a bi-directional multiplexer electrically coupled to the first electroporation electrode 102B of cell B and the second electroporation electrode 104B of cell B that is configured to fire a pulse to the first electroporation electrode 102B of cell B and/or the second electroporation electrode 104B of cell B.

A first sensing electrode 302B of cell B and a second sensing electrode 304B of cell B are also electrically separated by the substrate 106 and the liquid medium 130. The first sensing electrode 302B of cell B and the second sensing electrode 304B of cell B form polyhedral surfaces that are substantially orthogonal to the electrically insulated surface (e.g., on the x-y plane or y-z plane) of the substrate 106 and are not parallel to each other. In some examples, one or both of the polyhedral surfaces are curved. In some examples, one or both of the polyhedral surfaces are semi-circular or semi-elliptical. In some examples, one or both of the polyhedral surfaces are rectangular, triangular, or trapezoidal. In some examples, one or both of the polyhedral surfaces form a polyhedron situated on a cross-sectional end of the first sensing electrode 302B of cell B and/or the second sensing electrode 304B of cell B. In some instances, the polyhedron situated on a cross-sectional end of the first sensing electrode 302B of cell B and/or the second sensing electrode 304B of cell B forms a triangular prism, a quadrahedron, a pentahedron, a hexahedron, a septaheron, or an octahedron. In some instances, the polyhedron situated on a cross-sectional end of the first sensing electrode 302B of cell B and/or the second sensing electrode 304B of cell B forms a triangular prism, a quadrahedron, a pentahedron, a hexahedron, a septaheron, or an octahedron.

Although not depicted in FIG. 5, a signal generator 440 is electrically coupled to the first sensing electrode 302B of cell B and the second sensing electrode 304B of cell B, as depicted in FIG. 4A. The signal generator 440 can be a standalone signal generator electrically coupled to a microcontroller/computer. The electrical coupling between the standalone signal generator 440 and the microcontroller/computer can be a serial connector (e.g., universal serial bus (USB), serial port (RS-232 standard), Ethernet, FireWire, I2C, SPI, etc.) or a parallel connector (e.g., parallel port, enhanced parallel port (EPP), and extended capability port (ECP), etc.) or a general purpose interface bus (GPIB). In some examples, the signal generator 440 includes a bi-directional multiplexer electrically coupled to the first sensing electrode 302B of cell B and the second sensing electrode 304B of cell B that is configured to provide a signal to the first sensing electrode 302B of cell B and/or the second sensing electrode 304B of cell B.

It should be appreciated that in addition to cell A and cell B, the microelectrode probe array 500 can include additional cells that are similar to cell A and/or cell B. For example, although not depicted, the microelectrode probe array 500 can be expanded to include a cell C and/or a cell D, and/or a cell E, etc. In some examples, microelectrode probe array 500 is configured for electroporation of multiple individual cells or embryos and includes two or more of the microelectrodes of the microelectrode cells (e.g., microelectrode probe array 500). In such an instance, at least two of the two or more of the microelectrode cells are fluidly coupled (e.g., hermitically sealed) by a transport channel (e.g., microfluidic pipes 430). In some examples, microelectrode probe array 500 can be a microfluidic chip. That is, a microfluidic chip for electroporation of multiple individual cells or embryos 120 includes two or more of the microelectrode cells (e.g., microelectrode probe array 500). In such an instance, at least two of the two or more of the microelectrode cells are fluidly coupled (e.g., hermitically sealed) by a transport channel (e.g., microfluidic pipes 430).

As depicted in FIG. 5, a fluidic vent 108A of cell A extends into a sidewall 306A of cell A that is situated on the surface (e.g., on the x-y plane) of the substrate 106. The sidewall 306A of cell A extends vertically in a direction (e.g., positive z-direction) orthogonal to the insulated surface (e.g., on the x-y plane) of the substrate 106 and is a part of the microfluidic pipes 430. The vent 108A of cell A is smaller than the diameter of the cell or embryo 120 and is situated between the first electroporation electrode 102A of cell A and the second electroporation electrode 104A of cell A. In contrast to the vent 108 depicted in FIG. 4A, the surface of vent 108A of cell A is angled (in the x-y plane) with respect to the sidewall 306A and the surface of the vent 108A is orthogonal to the substrate 106. The angled surface at the vents 108 causes the cell or embryo 120 to position proximate to the substrate 106 so as to contact the sensing electrodes (e.g., first sensing electrode 302A of cell A and second sensing electrode 304A of cell A). In some examples, the entire the sidewall 306 is angled (e.g., non-orthogonal to the insulated surface (e.g., on the x-y plane) of the substrate 106). In some examples, the vents 108 are straight or rounded. In some examples, as shown in FIG. 4B, the vent 108 and the vent 108A may comprise a plurality of identical smaller vents 108C and 108D arranged in parallel or any angled configuration.

Likewise, a fluidic vent 108B of cell B extends into a sidewall 306B of cell B that is situated on the surface (e.g., on the x-y plane) of the substrate 106. The sidewall 306B of cell B extends vertically in a direction (e.g., positive z-direction) orthogonal to the insulated surface (e.g., on the x-y plane) of the substrate 106 and is a part of the microfluidic pipes 430. The vent 108B of cell B is smaller than the diameter of the cell or embryo 120 and is situated between the first electroporation electrode 102B of cell B and the second electroporation electrode 104B of cell B. Like vent 108A of cell A, the surface of vent 108B of cell B is angled (in the x-y plane) with respect to the sidewall 306A and the surface of the vent 108B is orthogonal to the substrate 106. The angled surface at the vents 108 causes the cell or embryo 120 to position proximate to the substrate 106 so as to contact the sensing electrodes (e.g., first sensing electrode 302B of cell B and second sensing electrode 304B of cell B). In some examples, the entire the sidewall 306 is angled (e.g., non-orthogonal to the insulated surface (e.g., on the x-y plane) of the substrate 106). In some examples, the vents 108 are straight or rounded. In some examples, as shown in FIG. 4B, the vent 108 and the vent 108B may comprise a plurality of identical smaller vents 108C and 108D arranged in parallel or any angled configuration.

Branches of microfluidic flow 332A within the channel 140A of cell A are continually constricted from one end of the channel 140A of cell A to the other end of vent A of cell A. The constriction increases the (liquid) current of the liquid medium 130 in the vent A of cell A. At the same time the constant constriction reduces the turbulent flow, which lessens eddy currents forming in channel 140A of cell A. In some examples, the decrease in eddy currents facilitates positioning the cell or embryo 120 on the first sensing electrode 302A of cell A and the second sensing electrode 304A of cell A.

In contrast, due to the polyhedral structure of the first electroporation electrode 102B of cell B and the second electroporation electrode 104B of cell B and/or the polyhedral structure of the first sensing electrode 302B of cell B and the second sensing electrode 304B of cell B, the channel 140B of cell B both narrows and widens. This narrowing and widening of the channel 140B of cell B causes the current of the branches of microfluidic flow 332B to increase (e.g., speed up) or decrease (e.g., slow down). This change in current in channel 140B of cell B increases the turbulent flow, which increases eddy currents forming in channel 140A of cell A. In some instances, the increase in eddy current facilitates positioning the cell or embryo 120 on the first sensing electrode 302A of cell A and the second sensing electrode 304A of cell A.

As depicted in FIG. 5, a pump 460 is hermetically coupled to the microfluidic pipes 430. The pump 460 is configured to adjust fluidic flow 330 in response to a PID 416 controller that is electrically coupled to the pump 460. The microfluidic pipes 430 are expanded in the vicinity of the pump 460. A larger impeller can drive more of the liquid medium 130 at a lower rotational velocity, which provides for a quieter pump. The fluidic flow 330 is adjusted in response to sensor data across the chip which allows a controller or computer to calculate velocity by identifying when liquid is at certain locations separated by known distances.

Figure 6:
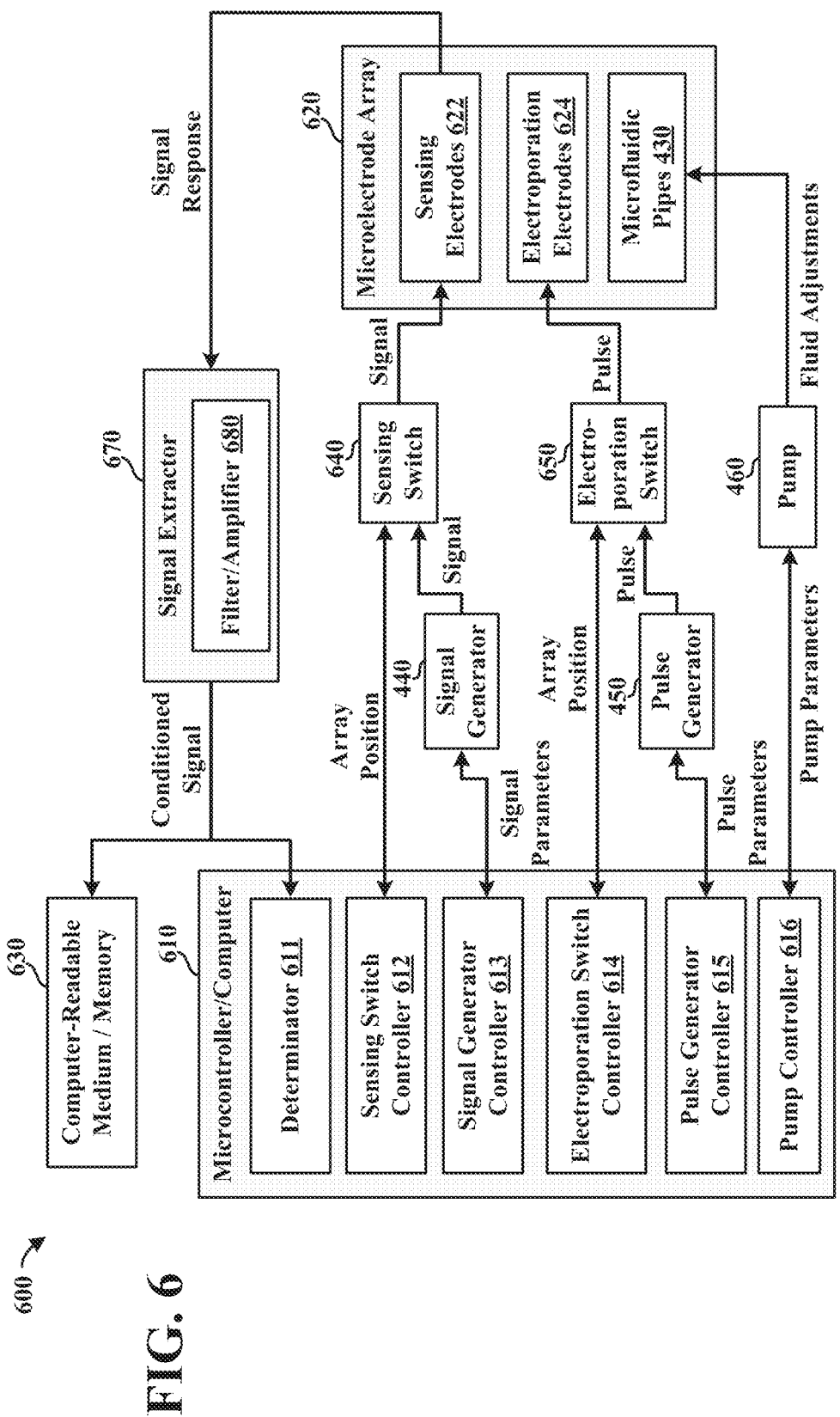
FIG. 6 is a conceptual data flow diagram illustrating the data flow between different hardware of an electroporation system.

FIG. 6 is a conceptual data flow diagram illustrating the data flow between different hardware of an electroporation system 600. The electroporation system 600 can be an integrated system with one or more various hardware components packaged together (e.g., on-chip) or a non-integrated system with one or more various hardware independent components or any combination thereof. For example, the computer-readable medium/memory 630 can be a separate and/or remote hardware component such as storage on a cloud server or memory (e.g., computer-readable medium/memory 630) integrated with microcontroller/computer 610 (e.g., on-chip). As depicted in FIG. 6, the electroporation system 600 includes a microcontroller/computer 610, a microelectrode array 620, a computer-readable medium/memory 630, a signal generator 440, a sensing switch 640, a pulse generator 450, an electroporation switch 650, a microfluidic pump 460, and a signal extractor 670.

The microcontroller/computer 610 includes one or more processors (e.g., cores) that are integrated with modules (e.g., input/output peripherals) and memory (e.g., cache, RAM, etc.) and capable of executing instructions of a program. The modules of the microcontroller/computer 610 are programmable input/output peripherals that interface with one or more modules of the microcontroller/computer 610 or with one or more electronic devices of the system (e.g., a signal generator 440, a sensing switch 640, a pulse generator 450, an electroporation switch 650, a microfluidic pump 460, etc.). As depicted in FIG. 6, the modules include a determinator 611, a sensing switch controller 612, a signal generator controller 613, an electroporation switch controller 614, a pulse generator controller 615, and a pump controller 616. It should be appreciated that some these modules can be integrated as hardware on-chip, while some of these modules can be implemented in software (e.g., firmware). It should be appreciated that the modules can include I/O circuitry to interface with one or more hardware components. The I/O circuitry can include a serial connector (e.g., universal serial bus (USB), serial port (RS-232 standard), Ethernet, FireWire, I2C, SPI) or a parallel connector (e.g., parallel port, enhanced parallel port (EPP), and extended capability port (ECP), etc.).

The determinator 611 is an input/output peripheral of the microcontroller/computer 610 that interfaces with the computer-readable medium/memory 630, the signal extractor 670, sensing switch controller 612, the signal generator controller 613, the electroporation switch controller 614, the pulse generator controller 615, and the pump controller 616. The determinator 611 determines various conditions in the electroporation system 600. For example, in some instances the determinator 611 receives a conditioned signal response (from a signal extractor 670) of a cell or embryo and compares it to an exemplary signal response of a cell or embryo stored in the memory (e.g., computer-readable medium/memory 630) to determine whether a membrane of a cell or embryo is permeable. (Block 712 of FIG. 7.) It should be appreciated the determinator 611 is programmable and therefore can be configured to determine one or more aspects of various cells or embryos. In some instances, the determinator 611 is configured to determine whether a characteristic of the conditioned signal response falls within a specific frequency range. In some instances, the determinator 611 is configured to determine whether a characteristic of the conditioned signal response within a specific frequency range exceeds a threshold. Programmability to accommodate specific characteristics of an exemplary signal response of a cell or embryo such as a voltage spike or a voltage level that exceeds a voltage threshold provides a more flexibility to characterize the permeability of various cells or embryos.

The sensing switch controller 612 is an input/output peripheral of the microcontroller/computer 610 that interfaces with the sensing switch 640. The sensing switch controller 612 provides one or more control parameters to the sensing switch 640 to designate a specific array position with the microelectrode array. The control parameters can be programmable bits that encode a cell position in the array. For example, the sensing switch controller 612 can include a programmable 8-bit control line encoded such that hexadecimal 00x (e.g., binary 00000000) electrically couples the signal generator 440 to the sensing electrodes 622 at cell A, hexadecimal 01x (e.g., binary 00000001) electrically couples the signal generator 440 to the sensing electrodes 622 at cell B, hexadecimal 1Ax (e.g., binary 00011010) electrically couples the signal generator 440 to the sensing electrodes 622 at cell Z, etc. In some examples, the sensing switch controller 612 includes one or more output registers of the microcontroller/computer 610 electrically coupled to control lines to signal sensing the switch 640 to route the signal.

The signal generator controller 613 is an input/output peripheral of the microcontroller/computer 610 that interfaces with the signal generator 440. The signal generator controller 613 provides one or more signal parameters for the signal generator 440 to generate a signal. The signal parameters can be frequency, wavelength, pulse duration, duty cycle, amplitude, wave type (e.g., sinusoidal, sawtooth, triangular, square, etc.), and duration between signals. In some examples, the signal generator controller 613 includes one or more output registers of the microcontroller/computer 610 to provide waveform parameters for the signal generator 440 to generate a signal.

As depicted in FIG. 6, the signal generator 440 is electrically coupled to the sensing electrodes 622 (e.g., first sensing electrode 302 and the second sensing electrode 304) via the sensing switch 640. The signal generator 440 is configured to inject a signal at one or both of the first sensing electrode 302 and the second sensing electrode 304. In some examples, it is possible for a signal to be addressed to the electroporating electrodes.

The sensing switch 640 is a switch that receives input from the sensing switch controller 612 to route a signal generated from the signal generator 440 to sensing electrodes 622 of the microelectrode array 620. In some examples, the sensing switch 640 is electrically coupled to the sensing electrodes 622 (e.g., first sensing electrode 302 and the second sensing electrode 304). The sensing switch 640 is configured to suppress an electric field perturbation between the first sensing electrode 302 and the second sensing electrode 304 in a first mode and provide an electric field between the first sensing electrode 302 and the second sensing electrode 304 in a second mode. In some instances, the sensing switch 640 is configured to toggle between the first mode and the second mode at predetermined periodicity. The predetermined periodicity can range from 100 µs to 50 ms. In some examples, the sensing switch 640 is a bi-directional multiplexer coupled to the sensing switch controller 612 and the signal generator 440 coupled to a microcontroller/computer. In some examples, the signal generator 440 and the sensing switch 640 form a switching circuit. In some instances, the switching circuit includes the signal generator 440 to form a mono-stable multi-vibrator.

The electroporation switch controller 614 is an input/output peripheral of the microcontroller/computer 610 that interfaces with the electroporation switch 650. The electroporation switch controller 614 provides one or more control parameters to the electroporation switch 650 to designate a specific array position with the microelectrode array. The control parameters can be programmable bits that encode a cell position in the array. For example, the electroporation switch controller 614 can include a programmable 8-bit control line encoded such that hexadecimal 00x (e.g., binary 00000000) electrically couples the pulse generator 450 to the electroporation electrodes 624 at cell A, hexadecimal 01x (e.g., binary 00000001) electrically couples the pulse generator 450 to the electroporation electrodes 624 at cell B, hexadecimal 1Ax (e.g., binary 00011010) electrically couples the pulse generator 450 to the electroporation electrodes 624 at cell Z, etc. In some examples, the electroporation switch controller 614 includes one or more output registers of the microcontroller/computer 610 electrically coupled to control lines to signal electroporation switch 650 to route a pulse to the electroporation electrodes 624. In some examples, the electroporation switch controller 614 is also simply a computer or microcontroller with a communication line to the pump.

The pulse generator controller 615 is an input/output peripheral of the microcontroller/computer 610 that interfaces with the pulse generator 450. The pulse generator controller 615 provides one or more pulse parameters for the pulse generator 450 to generate a pulse. The pulse parameters can be frequency, wavelength, pulse duration, duty cycle, amplitude, wave type (e.g., sinusoidal, saw-tooth, triangular, square, etc.), duration between pulses, etc. In some examples, the pulse generator controller 615 includes one or more output registers of the microcontroller/computer 610 to provide pulse parameters for the signal generator 440 to generate a pulse for the electroporation electrodes 624.

As depicted in FIG. 6, the pulse generator 450 is electrically coupled to the electroporation electrodes 624 (e.g., the first electroporation electrode 102 and the second electroporation electrode 104) via the electroporation switch 650. The pulse generator 450 is configured to inject a pulse at one or both of the first electroporation electrode 102 and the second electroporation electrode 104.

The electroporation switch 650 is a switch that receives input from the electroporation switch controller 614 to route a signal generated from the pulse generator 450 to the electroporation electrodes 624 of the microelectrode array 620. In some examples, the electroporation switch 650 is electrically coupled to the first electroporation electrode 102 and the second electroporation electrode 104. The electroporation switch 650 is configured to suppress an electric field between the surfaces (e.g., the first surface and the second surface) of the first electroporation electrode 102 and the second electroporation electrode 104 that are substantially orthogonal to the electrically insulated surface (e.g., on the x-y plane) of the substrate 106 in a first mode and provide an electric field between the surfaces (e.g., the first surface and the second surface) of the first electroporation electrode 102 and the second electroporation electrode 104 that are substantially orthogonal to the electrically insulated surface (e.g., on the x-y plane) of the substrate 106 in a second mode. In some instances, the electroporation switch 650 is configured to toggle between the first mode and the second mode at predetermined periodicity. In some instances, the electroporation switch 650 is configured to toggle between the first mode and the second mode at predetermined periodicity. The predetermined periodicity can range from 100 µs to 50 ms. In some examples, the electroporation switch 650 is a bi-directional multiplexer coupled to the electroporation switch controller 614 and the pulse generator 450 coupled to a microcontroller/computer. In some examples, the pulse generator 450 and the electroporation switch 650 form a switching circuit. In some instances, the switching circuit includes the pulse generator 450 to form a monostable multi-vibrator.

The pump controller 616 is an input/output peripheral of the microcontroller/computer 610 that interfaces with the microfluidic pump 460. The pump controller 616 provides one or more pump parameters for controlling the pump to adjust the flow of the fluid within the microelectrode array 620. The pump parameters include flow rate, start, stop, overshoot, dampening, etc. In some examples, the pump controller 616 is a proportional, integral, derivative (PID) algorithm controller.

As depicted in FIG. 6, the microelectrode array 620 includes sensing electrodes 622, electroporation electrodes 624, and microfluidic pipes 430. The sensing electrodes 622 of the microelectrode array 620 are electrically coupled to the sensing switch 640. The sensing electrodes 622 refer to the first sensing electrode 302 and the second sensing electrode 304, as depicted in FIGS. 3A, 3B, and 4 as well as to the first sensing electrode 302A of cell A and the second sensing electrode 304B of cell B, depicted in FIG. 5.

The electroporation electrodes 624 of the microelectrode array 620 are electrically coupled to the electroporation switch 650. The electroporation electrodes 624 refer to the first electroporation electrode 102 and the second electroporation electrode 104, as depicted in FIGS. 1A, 1B, 2A, 2B, 3A, 3B, and 4 as well as to the first electroporation electrode 102A of cell A and the second electroporation electrode 104B of cell B, depicted in FIG. 5.

The microfluidic pipes 430 of the microelectrode array 620 are hermetically coupled to the microfluidic pump 460. Various examples of the microfluidic pipes 430 are depicted in FIGS. 4 and 5.

As depicted in FIG. 6, the signal extractor 670 is electrically coupled to the sensing electrodes 622 and interfaces with the computer-readable medium/memory 630 and/or the determinator 611 of the microcontroller/computer 610. The signal extractor 670 is configured to capture a signal response from the injected signal of the signal generator 440 at the first sensing electrode 302 depicted in FIGS. 3A, 3B, and 4. This configuration can be expanded to a particular cell (e.g., cell A, cell B., etc.) of the microelectrode array for a first sensing electrode (302A, 302B), as depicted in FIG. 5. In some examples, the signal response at the second sensing electrode 304 (304A, 304B) in relation to the injected signal at the first sensing electrode 302 (302A, 302B) is proportional to the impedance of the cell or embryo 120. It should be appreciated that the signal extractor 670 can be electrically coupled to either the first sensing electrode 302 (302A, 302B) or the second sensing electrode 304 (304A, 304B) as long as the signal extractor 670 is interposed between an output of the signal generator 440 and only one of the sensing electrodes while the other the sensing electrode is shorted to ground, as depicted in FIG. 4A. That is, either the first sensing electrode 302 is electrically coupled to an output of the signal generator 440 and second sensing electrode 304 is shorted to ground or the second sensing electrode 304 is electrically coupled to an output of the signal generator 440 and first sensing electrode 302 is shorted to ground (e.g., FIG. 4A). In much the same way a sensing signal may be addressed to any electrode, the extractor may also pull information from any electrode.

The signal extractor 670 includes filter/amplifier 680 that can filter and/or amplify the signal response from the sensing electrodes 622 and provide a conditioned signal to the computer-readable medium/memory 630 and/or the determinator 611 of the microcontroller/computer 610. In some examples, the filter/amplifier 680 includes one or more low-pass filters configured to pass low frequency components of the response signal and attenuate high frequency components of the response signal. In some examples, the filter/amplifier 680 includes one or more high-pass filters configured to pass high frequency components of the response signal and attenuate low frequency components of the response signal. In some examples, the filter/amplifier 680 includes one or more band-pass filters or notch filters configured to pass a range of frequency components of the response signal and attenuate different range of frequency components of the response signal.

In some examples, the signal extractor 670 is configured to convert an analog response signal to a digital conditioned signal. For instance, in some examples the signal extractor 670 is an analog-to-digital converter. In some examples, the signal extractor 670 is configured as a balancing network such as a potentiostat or a galvanostat. In some instances, signal extractor 670 is a differential impedance matching network. In some examples, signal extractor 670 is an AC coupled bridge network. In some instances, signal extractor 670 is an auto-balancing bridge network.

Figure 7:
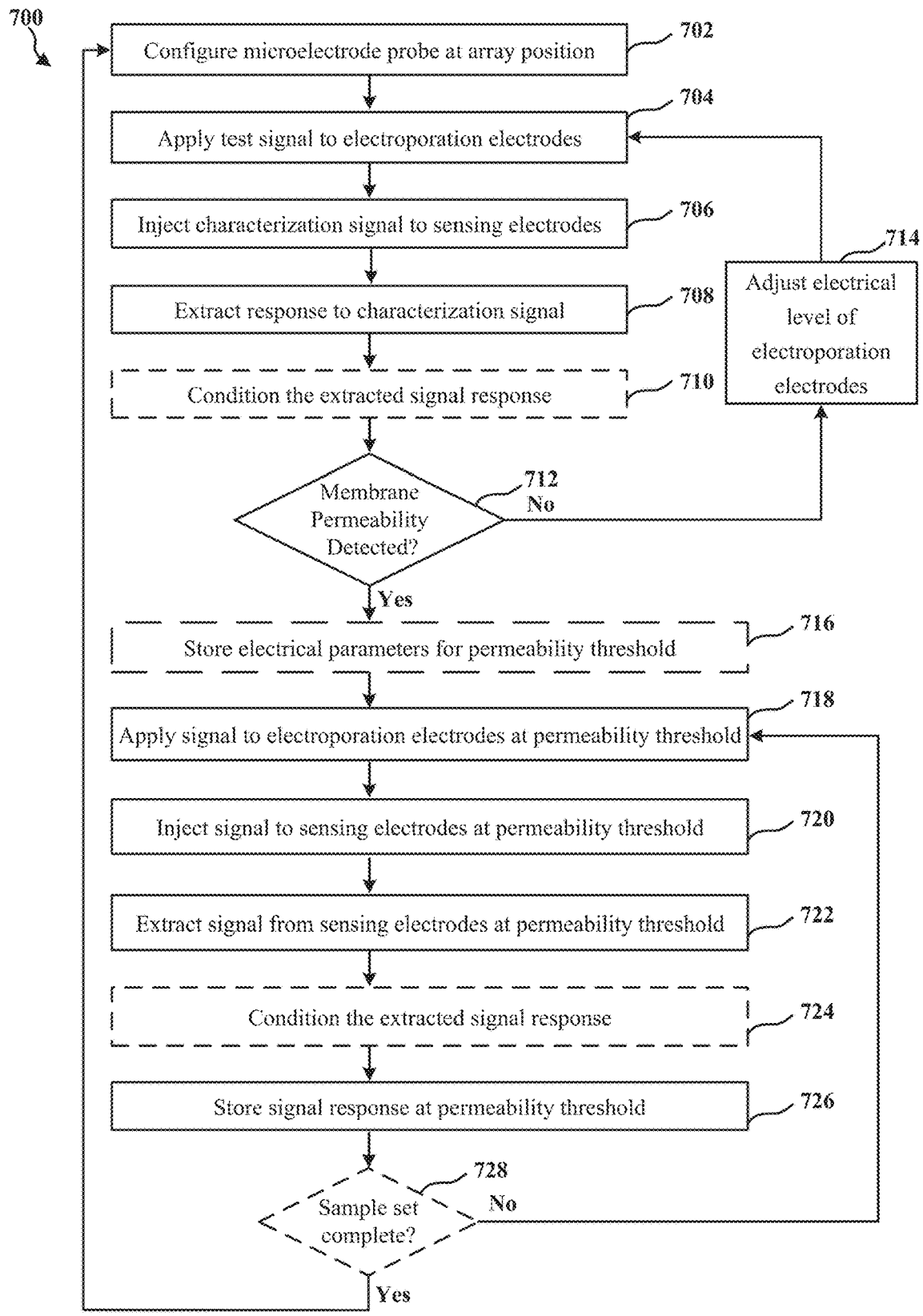
FIG. 7 illustrates an exemplary process for electroporation using a microelectrode probe in the microelectrode array.

FIG. 7 illustrates an exemplary process 700 for electroporation using a microelectrode probe in the microelectrode array 620. Process 700 can be performed by a system with one or more microelectrode probes arranged in an array (e.g., cell A, cell B of FIG. 5). Each pair of electroporation electrodes of a microelectrode probe in the array is electrically coupled to one or more switches that electrically couples the sensing electrodes 622 of a microelectrode probe to the signal generator 440 and electrically couples the electroporation electrodes 624 of a microelectrode probe to the pulse generator 450.

Referring to FIG. 6, the sensing switch controller 612 and the electroporation switch controller 614 of microcontroller/computer 610 configures at least one microelectrode probe at an array position so that the sensing electrodes 622 are electrically coupled to the signal generator 440 and the electroporation electrodes 624 are electrically coupled to a pulse generator 450, as depicted at block 702. In some examples, the sensing switch controller 612 and the electroporation switch controller 614 of microcontroller/computer 610 simultaneously trigger sensing switch 640 and electroporation switch 650, respectively. In response to the trigger, the sensing switch controller 612 signals sensing switch 640 electrically to couple the sensing electrodes 622 of a particular cell (e.g., cell A) to the signal generator 440. In response to the trigger, the electroporation switch controller 614 signals electroporation switch 650 to electrically couple the electroporation electrodes 624 of the same particular cell (e.g., cell A) to the pulse generator 450.

In some examples, the sensing switch 640 includes a bi-directional multiplexer electrically coupled to sensing electrodes 622 and one or both of the sensing switch controller 612 and the signal generator controller 613 of the microcontroller/computer 610 that triggers the bi-directional multiplexer to fire a signal to the sensing electrodes 622. In some examples, the sensing switch 640 is a switching circuit. In some examples, the switching circuit is a mono-stable multi-vibrator that includes the signal generator 440 with the sensing switch 640.

In some examples, the electroporation switch 650 includes a bi-directional multiplexer electrically coupled to electroporation electrodes 624 and one or both of the electroporation switch controller 614 and the pulse generator controller 615 of the microcontroller/computer 610 that trigger the bi-directional multiplexer to fire a pulse to the electroporation electrodes 624. In some examples, the electroporation switch 650 is a switching circuit. In some examples, the switching circuit is a mono-stable multi-vibrator that includes the pulse generator 450 with the electroporation switch 650.

Once the sensing switch 640 and the electroporation switch 650 are configured for a particular microelectrode probe at an array position, pulse generator controller 615 triggers pulse generator 450 to apply a test signal to the electroporation electrodes 624, as depicted at block 704 of process 700. The pulse generator controller 615 triggers the pulse generator 450 to apply a test signal (e.g., voltage signal or current signal) to the electroporation electrodes 624 of the particular cell (e.g., cell A) and induce an electric field between the first electroporation electrode 102 and the second electroporation electrode 104. The test signal to the electroporation electrodes 624 can be a generated voltage signal waveform or a generated electrical current signal waveform. The test signal to the electroporation electrodes 624 can be a sinusoidal or non-sinusoidal waveform. In some examples, the test signal includes pre-cursor or post-cursor FIR taps.

In some examples, the non-sinusoidal waveform of the test signal to the electroporation electrodes 624 is a square waveform, a triangular waveform, or a saw-tooth waveform. In some examples, the test signal to the electroporation electrodes 624 has a frequency between 133 Hz to 1 kHz. In some examples, the test signal to the electroporation electrodes 624 has a frequency between 1 Hz to 100 kHz. In some examples, the test signal to the electroporation electrodes 624 has a duty cycle of 50%. In some examples, the test signal can induce an electric field between the electroporation electrodes that ranges between 150 V/cm to 2 kV/cm. In some examples, the test signal can induce an electric field between the electroporation electrodes that ranges between 10 V/cm to 5 kV/cm.

While a test signal is applied to the electroporation electrodes 624 of the particular cell (e.g., cell A of FIG. 5), the signal generator controller 613 triggers the signal generator 440 to transmit a characterization signal to the sensing electrodes 622 of the particular cell (e.g., cell A of FIG. 5), which injects a current across the cell or embryo, as depicted at block 706. The characterization signal can be a sinusoidal or non-sinusoidal waveform. The characterization signal can be a generated voltage signal waveform or a generated electrical current signal waveform. In some examples, the non-sinusoidal waveform of the characterization signal is a square waveform, a triangular waveform, or a saw-tooth waveform. In some examples, the characterization signal to the sensing electrodes 622 has a frequency between 1 Hz to 1 MHz. In some instances, the characterization signal is piece wise. For example, in some examples, the characterization signal to the sensing electrodes 622 has a frequency between 1 Hz to 1 kHz and 50 kHz to 1 MHz. In some examples, the characterization signal to the sensing electrodes 622 has a frequency between 1 Hz to 1 kHz and 50 kHz to 100 GHz. In some examples, the characterization signal to the sensing electrodes 622 has a duty cycle of 50%.

At block 708 of process 700, the signal extractor 670 extracts the signal response from the characterization signal injected to the sensor electrodes. The signal response is the transference of electrical energy across the cell or embryo. As such, the signal response provides one or more electric characteristics of membrane permeability of the cell or embryo.

At optional block 710 of process 700, the filter/amplifier 680 of the signal extractor conditions the extracted signal response. The filter/amplifier 680 boosts and/or filters the signal response from the sensing electrodes 622 prior to transmitting the conditioned signal to the determinator 611 of the microcontroller/computer 610 or storing the conditioned signal to memory (e.g., computer-readable medium/memory). In some examples, conditioning the signal includes amplifying the extracted signal response. In such instances, the injected signal includes one or more frequencies.

It should be appreciated that various filters can be used. For example, the filter/amplifier 680 can be a low pass filter configured to pass low frequency components of the response signal and attenuate high frequency components of the response signal. In some examples, the filter/amplifier 680 is a high pass filter configured to pass high frequency components of the response signal and attenuate low frequency components of the response signal. In some examples, the filter/amplifier 680 is a band pass filter or a notch filter configured to pass a range of frequency components of the response signal and attenuate different range of frequency components of the response signal.

At block 712 of process 700, the determinator 611 attempts to determine whether the member of the cell or embryo is permeable. In process 700, the initial amplitude of the test signal is below a level that indices permeability of the membrane of the cell or embryo 120. By comparing the conditioned signal response (from a signal extractor 670) of a cell or embryo 120 with an exemplary signal response of a cell or embryo 120 stored in the memory (e.g., computer-readable medium/memory 630), the determinator 611 can determine whether a membrane of a cell or embryo 120 is permeable. In some examples, the determinator 611 can determine whether a membrane of a cell or embryo 120 is permeable based on whether a characteristic of the conditioned signal response within a specific frequency range exceeds a threshold value (e.g., permeability threshold).

In accordance with a determination that a membrane of a cell or embryo is not permeable, the determinator 611 triggers the pulse generator controller 615 to adjust the electrical levels of the test signal applied to the electroporation electrodes 624, as depicted at block 714 of the process 700. In turn, the process 700 re-applies a test signal at the adjusted electrical levels to the electroporation electrodes, back at block 704. As depicted in FIG. 7, process 700 continues to iteratively loop blocks 704 through 714, which adjusts the electrical levels (e.g., steps the voltage) of the test signal applied to the electroporation electrodes 624 with each iteration until the determinator 611 determines that a membrane of a cell or embryo is permeable (e.g., a permeability threshold is exceeded).

In accordance with a determination that a membrane of a cell or embryo is permeable (e.g., a permeability threshold is exceeded), the determinator 611 stores the electrical parameters for the permeability threshold in computer-readable medium/memory 630, as depicted at optional block 716.

At block 718 of process 700, the pulse generator controller 615 triggers pulse generator 450 to apply a signal (e.g., voltage to induce an electric field) to the electroporation electrodes 624 at the permeability threshold. The generated electrical pulse or signal to the electroporation electrodes 624 should reflect the test signal to the electroporation electrodes 624. It should be appreciated that the duration of the applied signal to the electroporation electrodes 624 can vary. In some examples, the duration of the applied signal to the electroporation electrodes 624 is 10 ms. In some examples, the duration of the applied signal to the electroporation electrodes 624 is in the range from 1 ms to 100 ms, particularly 1 ms, 2 ms, 5 ms, 12 ms, or 15 ms. In some examples, the duration of the applied signal to the electroporation electrodes 624 is 20 ms. In some examples, the signal includes five pulses that are separated by 100 ms. In some examples, the signal selected from a range of 1-10 pulses that are separated by 25-200 ms. In some examples, the separation between pulses range from 10 ms to 60 s.

While the signal is applied to the electroporation electrodes 624 of the particular cell (e.g., cell A), the signal generator controller 613 triggers the signal generator 440 to transmit the signal (e.g., voltage signal or current signal) to the sensing electrodes 622 of the particular cell (e.g., cell A), which injects a current across the cell or embryo at the permeability threshold, as depicted at block 720. The generated electrical pulse or signal to the sensing electrodes 622 should reflect the characterization signal to the sensing electrodes 622.

At block 722 of process 700, the signal extractor 670 extracts the signal response from the signal injected to the sensor electrodes. The signal extractor 670 used for the signal at the permeability threshold should reflect the signal extractor 670 used for the characterization signal.

At optional block 724 of process 700, the filter/amplifier 680 of the signal extractor 670 conditions the extracted signal response. In some examples, conditioning the signal includes amplifying the extracted signal response. In such instances, the injected signal includes one or more frequencies. In general, the filter/amplifier 680 of the signal extractor 670 used for the signal response at the permeability threshold should reflect the filter/amplifier 680 of the signal extractor 670 used for the characterization signal.

At block 726 of process 700, the signal extractor 670 stores the conditioned signal response and/or the signal at the permeability threshold to memory (e.g., computer-readable medium/memory).

At optional block 728 of process 700, the signal determinator 611 determines whether the sample set is complete. In accordance with a determination that the sample set is not complete, process 700 loops back to block 718 to re-apply the signal at permeability threshold at the same microelectrode probe (e.g., same cell in the array). In accordance with a determination that the sample set is complete, process 700 can optionally change cells in the array and loop back to block 702 and reconfigure a new microelectrode probe at a new array position (e.g., different cell in the array).

It is understood that the specific order or hierarchy of blocks in the processes/flowcharts disclosed is an illustration of exemplary approaches. Based upon design preferences, it is understood that the specific order or hierarchy of blocks in the processes/flowcharts can be rearranged. Further, some blocks can be combined or omitted. The accompanying method claims present elements of the various blocks in a sample order, and are not meant to be limited to the specific order or hierarchy presented. Any processes or algorithms presented are merely exemplary and are not intended to limit the scope of disclosure; one skilled in the art may find alternative processes or algorithms that accomplish the same tasks as described herein.

The previous description is provided to enable any person skilled in the art to practice the various examples described herein. Various modifications to these examples will be readily apparent to those skilled in the art, and the generic principles defined herein can be applied to other examples. Thus, the claims are not intended to be limited to the examples shown herein, but are to be accorded the full scope consistent with the language of the claims, wherein reference to an element in the singular is not intended to mean "one and only one" unless specifically so stated, but rather "one or more." The word "exemplary" is used herein to mean "serving as an example, instance, or illustration." Any example described herein as "exemplary" is not necessarily to be construed as preferred or advantageous over other examples. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and can include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" can be A only, B only, C only, A and B, A and C, B and C, or A and B and C, where any such combinations can contain one or more member or members of A, B, or C. All structural and functional equivalents to the elements of the various examples described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like cannot be a substitute for the word "means." As such, no claim element is to be construed under 35 U.S.C § 112(f) unless the element is expressly recited using the phrase "means for."

What is claimed is:

1. A viability sensing system comprising:
   a microelectrode comprising:
   a substrate with an electrically insulated surface;
   a first electrode adjacent to the electrically insulated surface of the substrate, wherein the first electrode includes a first surface with an edge length that is less than or equal to a diameter of the cell or embryo, the first surface being substantially orthogonal to the electrically insulated surface of the substrate;
   a second electrode adjacent to the electrically insulated surface of the substrate and separated from the first electrode a predetermined distance so as to form a channel between the first electrode, the second electrode, and the electrically insulated surface of the substrate, wherein the second electrode includes a second surface with an edge length that is less than or equal to a diameter of the cell or embryo, the second surface being substantially orthogonal to the electrically insulated surface of the substrate; and
   a liquid medium situated within the channel, wherein the first electrode, the second electrode, and the electrically insulated surface of the substrate are configured so that the liquid medium is capable of fluidic transport of the cell or embryo through the channel between the first electrode, the second electrode, and the electrically insulated surface of the substrate and capable of supporting an electric field, wherein the second surface is substantially parallel to the first surface and the first electrode and the second electrode are configured to generate a uniform electric field with substantially parallel electric field lines between the first surface and the second surface; and
   a first signal generator electrically coupled to the first electrode and the second electrode, wherein the first signal generator is configured to generate a signal between the first electrode and the second electrode that induces a uniform electric field with substantially parallel electric field lines between the first surface and the second surface, and wherein a sensing signal is received by either the first electrode or the second electrode, wherein the generated signal optionally is a sinusoid waveform or a nonsinusoidal waveform, optionally, an exponential waveform, a square waveform, a triangular waveform, or a saw-tooth waveform, optionally has a frequency between 1 Hz to 100 GHz or between 1 Hz to 1 kHz 100 GHz, and/or optionally has a duty cycle of 50%, and the induced electric field optionally ranges between 10 V/cm to 5 kV/cm or between 100 V/cm to 4 kV/cm.

2. The viability sensing system of claim 1, further comprising:
   a third electrode adjacent to the electrically insulated surface of the substrate; and
   a fourth electrode adjacent to the electrically insulated surface of the substrate, wherein the third electrode and the fourth electrode are situated adjacent to the channel or within the channel to accommodate electrical contact between the third electrode and the fourth electrode and the cell or embryo; and
   a differential amplifier electrically coupled to the third electrode and the fourth electrode, wherein the second signal generator is configured to inject a signal at any of the first, second, third, or fourth electrodes and optionally a signal extractor electrically coupled to the fourth electrode, wherein the signal extractor is configured to capture a signal response from the injected signal at any of the first, second, third, or fourth electrodes and optionally the signal response at the fourth electrode in relation to the injected signal at any of the first, second, third, or fourth electrodes is proportional to the impedance of the cell or embryo or the signal extractor is an analog-to-digital converter, a potentiostat, a galvanostat, a differential impedance matching network, an AC coupled bridge network, or an auto-balancing bridge network.

3. The microelectrode of claim 1, wherein the first electrode includes a third surface adjacent to first surface and the electrically insulated surface of the substrate, and wherein the second electrode includes a fourth surface adjacent to first surface.

4. The microelectrode of claim 1, wherein the edge length of one or both of the first surface and the second surface ranges from 0.02% to 75.0% of the diameter of the cell or embryo.

5. The microelectrode of claim 1, wherein one or both of the first electrode and the second electrode are deposited on the electrically insulated surface using techniques selected from the group consisting of physical vapor deposition, chemical vapor deposition, electroplating, and/or wet etching and/or are made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy, graphene, indium tin oxide, tin, ruthenium, ruthenium oxide, rhodium, zirconium, TiNi, Al—Si—Cu, and cobalt.

6. The microelectrode of claim 1, wherein one or both of the first electrode and the second electrode include a hydrophilic surface coating.

7. The microelectrode of claim 1, wherein one or both of the first electrode and the second electrode are made from a conductive alloy.

8. The microelectrode of claim 1, wherein the channel is configured to isolate the cell or embryo between the first surface and the second surface.

9. The microelectrode of claim 1, wherein the substrate includes one or more fluidic vents situated within the electrically insulated surface of the substrate between the first surface and the second surface or the substrate includes one or more fluidic vents situated within a second electrically insulated surface of the substrate between the first surface and the second surface, wherein the second electrically insulated surface of the substrate is orthogonal to both the electrically insulated surface of the substrate and the first surface, wherein the one or more fluidic vents are optionally smaller than the diameter of the cell or embryo and/or optionally the liquid medium flows through the one or more vents and positions the cell or embryo within the channel between the first electrode and the second electrode.

10. The microelectrode of claim 1, further comprising a second substrate with a second electrically insulated surface situated above the channel, wherein the second electrically insulated surface is substantially parallel to the first electrically insulated surface and is separated from the first electrically insulated surface a second predetermined distance that is 100% to 250%, 50% to 200%, 50% to less than 100%, or 10% to 50% of the diameter of the cell or the embryo to position the cell or embryo within the channel between the first electrode and the second electrode.

11. The microelectrode of claim 1, further comprising: a third electrode adjacent to the electrically insulated surface of the substrate; and a fourth electrode adjacent to the electrically insulated surface of the substrate, wherein the third electrode and the fourth electrode are situated adjacent to the channel or within the channel to accommodate electrical contact between the third electrode and the fourth electrode and the cell or embryo, wherein cross-sections of one or both of the third electrode and the fourth electrode are optionally rectangular, triangular, trapezoidal, semi-circular, or semi-elliptical; an edge length of one or both of the third electrode and the fourth electrode is optionally less than the edge length of the first surface or the second surface and/or ranges optionally from 100 nm to 3.3 µm; and/or one or both of the third electrode and the fourth electrode optionally include a hydrophilic surface coating, optionally are made from a material selected from the group consisting of polysilicon, aluminum, nickel, tungsten, copper, titanium, nichrome, silicon chrome, chromium, molybdenum, platinum, gold, silver, palladium, TiW, titanium nitride, tantalum nitride, vanadium, permalloy (NiFe), graphene, indium tin oxide, tin, ruthenium, ruthenium oxide, rhodium, zirconium, TiNi, Al—Si—Cu, and cobalt, and/or optionally are made from a conductive alloy.

12. The microelectrode of claim 1, wherein the liquid medium includes a polynucleotide with a concentration ranging between 1 ng/µL to 10 mg/µL or between 1 ng/µL to 10 µg/µL, and the polynucleotide is optionally a polyribonucleotide optionally in complex with a polypeptide.

13. The microelectrode of claim 1, wherein the substrate is glass (optionally, Pyrex 7740, BK7 glass, Borofloat 33, Corning Eagle glass, D263, Gorilla glass, and sodalime glass), silicon, fused silica quartz or single crystal quartz, silicon-on-insulator (optionally, selected from the group consisting of silicon nitride on silicon and siliconoxide on silicon), germanium, germanium-on-insulator, zinc oxide, a polymer (optionally, selected from the group consisting of Cast acrylic, ABS, nylon, polyethylene, cyclic olefin copolymer and polymer, acetal, polycarbonate, PETG, polyimide, FEP, PTFE, Polystyrene, polypropylene, silicone, PVC, polyurethane, PMMA, and PDMS), polydimethylsiloxane, low-temperature co-fired ceramic, or positive or negative photoresist.

14. A method of sensing the viability of an individual cell or embryo with a microelectrode comprising a first electrode, a second electrode, a third electrode, and a fourth electrode, the method comprising:
applying a first test signal between the first electrode and the second electrode at a predetermined electrical energy level;
extracting, at the third electrode and fourth electrode a differential voltage measurement;
determining whether the response to the first test signal is characteristic of cell volume, membrane permeability, or cytoplasm conductivity of the cell or embryo; and
in accordance with a determination that the response is characteristic of viability of the cell or embryo, storing electrical parameters associated with the predetermined electrical energy level, and optionally conditioning the extracted second test signal response optionally by including one or more low pass filters and/or amplifying the extracted signal response.

* * * * *